US008617469B2

(12) United States Patent
Vlahovic et al.

(10) Patent No.: US 8,617,469 B2
(45) Date of Patent: Dec. 31, 2013

(54) NANOSTRUCTURE BASED METHODS FOR DETECTION STRUCTURE DETERMINATION SEPARATION TRANSPORT EXTRACTION AND CONTROL OF CHEMICAL AND BIOCHEMICAL MATERIAL

(76) Inventors: Branislav Vlahovic, Chapel Hill, NC (US); Vanja Vlahovic Malloy, Chapel Hill, NC (US)

( * ) Notice: Subject to any disclaimer, the term of this patent is extended or adjusted under 35 U.S.C. 154(b) by 0 days.

(21) Appl. No.: 13/607,826

(22) Filed: Sep. 10, 2012

(65) Prior Publication Data

US 2013/0012414 A1  Jan. 10, 2013

Related U.S. Application Data

(62) Division of application No. 10/907,819, filed on Apr. 15, 2005, now Pat. No. 8,262,998.

(51) Int. Cl.
*G01N 33/00* (2006.01)
(52) U.S. Cl.
USPC .......... 422/82.01; 422/50; 422/401; 422/402; 422/82.02; 422/82.05; 422/82.06; 422/82.07
(58) Field of Classification Search
USPC .......... 422/82.01, 50, 401, 402, 82.02, 82.05, 422/82.06, 82.07
See application file for complete search history.

(56) References Cited

U.S. PATENT DOCUMENTS

| 7,129,554 B2 * | 10/2006 | Lieber et al. ................... 257/414 |
| 8,262,998 B2 * | 9/2012 | Vlahovic et al. ............ 422/82.01 |
| 2002/0172820 A1 * | 11/2002 | Majumdar et al. ............ 428/357 |
| 2003/0030067 A1 * | 2/2003 | Chen ............................. 257/102 |
| 2003/0047816 A1 * | 3/2003 | Dutta ............................ 257/788 |
| 2003/0099279 A1 * | 5/2003 | Venkatasubramanian et al. ............................. 374/179 |
| 2003/0109056 A1 * | 6/2003 | Vossmeyer et al. ........... 436/169 |
| 2004/0029288 A1 * | 2/2004 | Snow et al. ................... 436/149 |

* cited by examiner

*Primary Examiner* — Sam P Siefke
(74) *Attorney, Agent, or Firm* — Vanja Vlahovic; Branislav Vlahovic

(57) ABSTRACT

The invention describes methods that use nanostructures and quantum confinement to detect and manipulate chemical and biochemical molecules. To increase selectivity and sensitivity nanostructures are built to have the density of states similar to that in analyte that will be detected and operated. Using device that incorporates such nanostructures, measuring electrical and optical properties of nanostructures and analyte or charge and energy transfer between the nanostructures and analyte a rapid and sensitive continuous detection in fluids can be achieved. Detection can be further enhanced by controlling external environmental parameters and applying external fields. In addition to be detected analyte can be positioned, moved, separated, extracted, and controlled.

17 Claims, 22 Drawing Sheets nanostructure analite a)

b)

nanostructure    analite

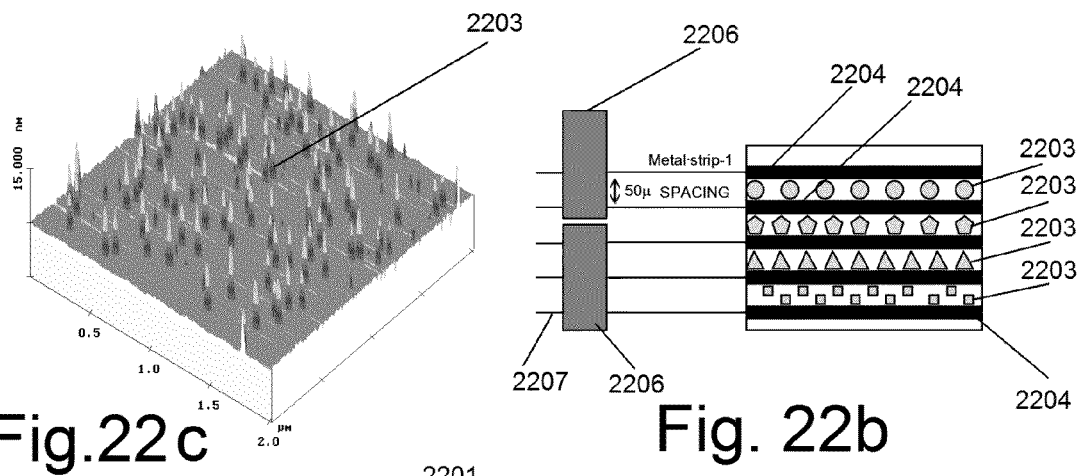
Fig.22c
Fig. 22b
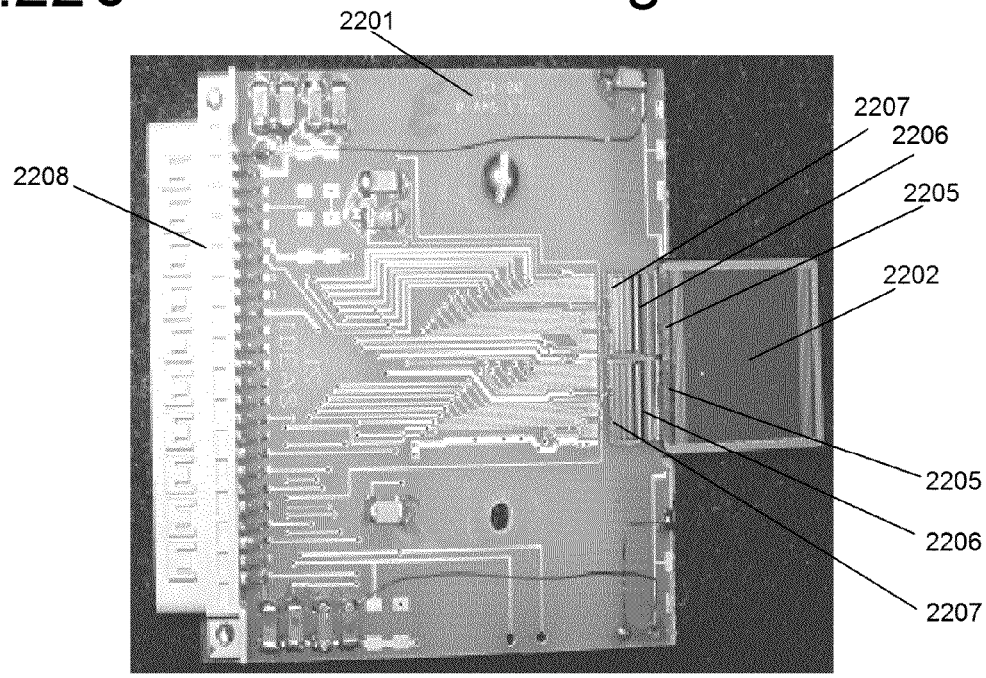
Fig. 22a

# NANOSTRUCTURE BASED METHODS FOR DETECTION STRUCTURE DETERMINATION SEPARATION TRANSPORT EXTRACTION AND CONTROL OF CHEMICAL AND BIOCHEMICAL MATERIAL

RELATED APPLICATIONS

This is a Divisional of patent application Ser. No. 10/907,819, filed on Apr. 15, 2005, now projected U.S. Pat. No. 8,262,998.

FIELD OF THE INVENTION

Invention relates to the methods and apparatus for detection and determination of structure and/or composition of chemical and/or biological materials or molecules. The invention also relates to transport, manipulation, separation and extraction of the biological and chemical materials. It transcends several scientific disciplines, physics, chemistry, biology, and medicine, but the base of the method is charge or energy transfer that increases if the structures and analyte have overlapping energy levels and state densities.

THE BACKGROUND

A variety of methods and sensors have been developed for chemical, biochemical, biological or biochemical analysis, control and detection. Biological species of interest include molecules, for example: sugars, nucleic acids, proteins, DNA, RNA, various toxins, bacteria, parasites, fungi, viruses, etc. The development of the claimed detection methods will have significant impact on broad range of applications related to medical diagnostic, drug development, food control and safety, the environment, energy production, and security. However, the invention has even broader range of applicability. Development of new nanostructured materials together with the emerging advances in micro, nano and superlattice structures and electronics create a new avenue for construction of more advanced methods and sensors.

There exist a number of known methods for detecting biochemical materials. The most common are: optical absorption and reflection, Raman spectroscopy, photoluminescence, fluorescence, electrophoresis, mass spectroscopy, ion mobility etc. The current generation of sensors is mostly constructed of a transducer in combination with a biological active surface. Many of these rely on specific ligand antiligand reactions as the detection mechanism. Others rely on electronic signals for detection, using DC or AC potentials, and detecting change in impedance, with or without using mediators for charge transfer to the electrode.

Ideally, the sensors should be sensitive (low detection limits) and specific. For the gene probe, the extent of molecular complementarity between probe and target defines the specificity. In general, it is very difficult to obtain a perfect complementarity for targets with mismatches, since small variations in reaction conditions will alert the hybridization. It would be desirable to detect single molecule binding events with the specificity of a single base pair mismatch of a DNA.

Novel functional materials such as superlattice structures, quantum dots, nanowires, nanotubes, porous membranes, with or without attached functional groups, have been used as a sensing elements in combination with various possible detection mechanisms.

Some of the techniques take the advantage of the lengthwise similarity between the thickness of the superlattice layer and typical distance between bonding sites of biological and chemical molecules as well as between overall thickness of the superlattice structure and the length of such biological and chemical molecules. The surface binding of the biomolecules on the superlattice has been achieved by activating the superlattice by optical illumination or by electrical biasing; see for instance P. D. Brewer et al. US patent application publication US20050042773A1.

The other example of using the combination of the nanostructure, functionalized or not functionalized, and the spacing between the electrodes is a modified time of flight experiment. The ionic current is measured when the voltage biases are applied across the nanocapillary or nanotube. The electrophoretical flow of a single stranded polynucleotides through the structure blocks and reduces the ionic current. Time of flight of these polynucleotides vary linearly with their length, and different nucleotides will have different blocking signals, which will allow one to rapidly sequence the DNA (P. Yang et al. US patent application publication US20040262636A1).

There are also other devices where one or more voltage sources are coupled to each of the plurality of nano or micro sized regions on the semiconductor substrate. The one or more voltage sources selectively apply voltage to any one or more of the plurality of nano or micro sized regions to attract a particular molecule species to the one or more of the plurality of nano or micro sized regions (K. Code et al. US patent application publication US20050032100A1).

In one embodiment, complementary and non-complementary DNA is differentiated by measuring conductivity. Glass surface between two golden electrodes is modified by oligonucleotides complementary to the target DNA. Only complementary target DNA strands form nanoparticle assemblies between the two electrodes, and complete circuit by nanoparticle hybridization. This format is extended to substrate array, chips, with thousands of pairs of electrodes capable of testing for thousands of different nucleic acids (C. A. Mirkin et al. U.S. Pat. No. 6,828,432B2).

Active microelectronic arrays that use DC and AC fields for transport and positioning of biochemical molecules, DNA, biological cells, antibodies, polymers, etc. are fabricated with 25 to 10,000 test sites or micro-locations. An example is 100 test site chip commercialized by Nanogen, from San Diego, Calif. The chip has 80 microns diameter test sites/microlocations with underlying platinum microelectrodes, and twenty auxiliary outer microelectrodes. The outer group of microelectrodes provides encompassing electric field for concentrating charged particles in the active test area. On the similar device fluorescent nucleic acid molecules which are about 7 nm in length were transported back and forth over a distance of about 200 microns (K. Code et al. US patent application publication US20040158051A1).

There are many other applications of nanostructures, quantum dots, nanowires, nanotubes and superlattices for detection of biochemical molecules. However, their common characteristic is that they do not use quantum confinement in the sense it is applied in this invention. In all of the other applications, when used, the quantum confinement is related only to the optical detection methods. One of the examples is the selective infrared detection, where only the photons with energies equal to the difference of the energy levels can excite electrons. Another frequent quantum confinement application has been to eliminate energy momentum dispersion and to decrease phonon scattering rate and increase internal gain in a quantum dot based inter-sub band photoconductor (K. Code et al. US patent application publication US20040256612A1). The other application uses quantum dots that are substantially defect free, so that quantum dots exhibit photoluminescence with a quantum efficiency that is greater then 10 percent (H. W. H. Lee et al. US patent application publication US20050017260A1). In addition, there are number of sensors that rely on the use of particles and quantum dots, including magnetic particles, particularly for electrochemiluminescence detection (K. Code et al. U.S. Pat. No. 5,746,974; U.S. Pat. No. 5,770,459). Very recently the AlGaN/GaN heterostructures have been predicted to act as efficient biosensors detecting pH values of electrolytes, provided the two-dimensional electron gas lies close to the Ga oxide layer as in the case for N-face heterostructures (M. Bayer, C. Uhl, and P. Vogl, J. Appl. Phys. 97, 033703 (2005)). However, as it was said above, all of the examples enumerated do not use quantum confinement in a straight way applied in this invention.

BRIEF SUMMARY OF THE INVENTION

Our invention is based on comparison of the distributions of density of states (distribution of the energy levels plus the probability that charges occupy the energy levels) in detector nanostructures and analyte that will be detected. By specific design of nanostructures (size, shape, composition) and external parameters (applied AC or/and DC bias, electromagnetic radiation, pressure, magnetic fields, temperature, stress, etc.) we are controlling the density of states in detector nanostructures, and making it similar or different from the density of states in the analyte. If density of states in nanostructures is similar to that in analyte (if it overlaps with that in analyte) the charge or energy transfer between the analyte and detector nanostructure will happen. If it is not similar the charge or energy transfer between nanostructures and analyte will not happen. If the charge transfer is registered by the electronics part of the apparatus, it means that specific analyte (that has the same density of states as nanostructure) is close to the nanostructure. If some other analyte (with different density of states, different than in nanostructure) is close to the nanostructure the charge or energy transfer will not happen. So by controlling density of state in nanostructures, which is done by controlling design and external parameters, we are controlling which analyte will be targeted, recognized, detected and further selected, controlled and/or extracted. An additional set of external parameters (DC or AC bias, that may be continuous or pulsed, and have different ranges of intensity and/or frequency and/or magnetic fields, temperature, electromagnetic radiation, or their combination) can be applied on detected sample to further select, control and manipulate it (for instance move it, separate it, extract it).

The present invention pertains to the new biochemical detection methods, based on the quantum confinement effect, which may significantly benefit broad range of applications in science, health care, diagnostics, prognostics, security and safety. Over the years, various molecular detection techniques have been developed. This invention provides significant improvement in the sensitivity, specificity, cost reduction, device miniaturization, and time required for the detection. It also provides new way to select, move, transport, separate, extract, and control analyte.

Before giving the specifics of the invention, it will be beneficiary to compare it with the progress that the optical spectroscopy brought to the development of the detection methods. Before the development of the optical spectroscopy it was possible to obtain only limited information about the material by optical measurements, for instance, transparency, absorbance, and color. However, the real progress in optical measurements has been made only after establishment of the spectroscopic methods which include measurements of the atomic and molecular spectrum, and measurement of spectral emission and absorption lines. We claim that the proposed invention will bring similar order of magnitude improvement in detection specificity and selectivity.

Many methods have been developed which are based on measuring changes in the electrical current between the electrodes, caused by the presence of the specific analyte. Some of the methods are using nanoparticles and electrodes, measuring the change in the electrical current or electrical signals when analyte with the attached nanoparticle is present. In other cases the electrodes or the nanoparticles are functionalized to attract the specific analyte. However, all these methods are missing specificity, as the optical method missed it before the measurements of the spectral lines were applied.

This invention is also based on the measurement of the charge and/or energy transfer between the nanostructures and the analytes; however, there is substantial difference between this and the existing methods. In this invention nanostructures are designed to create specific quantum confinement, in such a way that the density distribution of the energy levels in the nanostructures matches the density energy levels distribution in the analyte. If the analogy with the optical spectroscopy is used again, only the photons which have the same energy as the energy levels separation in the analyte will be absorbed or emitted. Similarly, in the present invention, the charge and/or energy transfer between the nanostructure and targeted analyte will occur only when the electronic density of states in the detectors nanostructures is the same as the density of states in the analyte. This significantly increases sensitivity, selectivity and specificity of the analyte detection, since different analytes have different combination of the density energy levels distributions (similarly as the different analyte have different combination of the spectral lines).

The nanostructure part of the detector device may be built, for instance, from quantum dots. The size and other parameters of the quantum dots can be chosen so that the three dimensional charge confinement of quantum dots creates specific energy levels designed to match the energy levels in the specific targeted analyte. The device may further contain other quantum dots with the other energy levels. In principle it may contain thousands of different kinds of quantum dots for detecting thousands of different analytes. Detection of the charge transfer or the absence of the charge transfer from the specific quantum dots will give confirmation of presence or absence of specific targeted analyte.

In addition to having the nanostructure with the specific energy levels, the separation between the quantum dots also may be chosen to match the length similarity with the charge distribution in the analyte. Knowing the density of states distribution in the analyte, the separation or distance between the charges and the amount of the charges the complete distribution of the charge of the analyte may be determined.

In the above described device, the use of the quantum dots is chosen just as an example. The nanostructures which are used to build the device sensing element may be for instance superlattice structures, where the thickness and the area of the superlattice determine the quantum confinement and the density of states distribution of the analyte.

The device can be also built from nanowires, nanotubes or any other nanostructure, where again the volume of the nanotube, nanowire or any chosen nanostructure is such that the density of states distribution in the nanostructures, created by quantum confinement, mimics the density of energy levels distribution in the specific analyte.

The nanotube or nanowire, or in general any nanostructure, may be composite, and may be built from several isolated nanotubes, nanowires or nanostructures, which are all combined to make one large nanotube, nanowire or nanostructure.

Having the above examples in mind, it is obvious that by using different nanostructures different resolution of the devices may be achieved. Superlattice materials, which are again taken here just as an example, may be chosen when the charge transfer with a resolution of a few Angstroms is required. The quantum dots and quantum wires may be chosen to obtain resolutions from a few nanometers to up to a few microns. So, the fine or coarse charge resolutions of biochemical molecules, proteins, amino acids, bacteria, viruses, etc. can be obtained by applying appropriate nanostructures or appropriate combination of nanostructures.

The charge and/or energy transfer between the device and nanostructures and/or between the nanostructure elements may be initiated or modified by external electrical field, applied voltage bias, applied light, applied electromagnetic field, magnetic fields, temperature or the combination of these factors. The applied external effects may be DC or AC, they may be continuous or pulsed, and intensity and/or frequency of electric fields, magnetic fields, temperatures, light or their combination may be in a broad range and may change during the time. The external fields may be designed to have the effect on the nanostructure confinement charge energy levels and/or to excite the energy states of the targeted analyte and/or to activate the charge transfer. An additional set (different form that applied to make desired density of state) of external fields, AC, DC, pressure, temperature, magnetic fields, etc. may be applied to manipulate and control analyte.

The device nanostructure may or may not be functionalized by the attachment of specific biochemical groups, molecules, atoms, proteins, or antibodies; that will attract or repeal the specific atoms, molecules, groups or antibodies which are complementary or the same as in the analyte and are in some way characteristic for the specific analyte.

BRIEF DESCRIPTION OF THE SEVERAL VIEWS OF THE DRAWING

The invention will be better understood by reference to the following drawings which are for illustrative purpose only:

FIG. 6 shows the change of the electron energy levels inside the quantum ring shaped quantum dots.

In FIG. 8c the density of states of a nanostructure (806) and density of states of an analyte (807) overlap and between these structures will be charge/energy transfer. In FIG. 8d the densities of states of nanostructure (808) and analyte (809) do not overlap and there will be no energy charge/energy transfer. Only when the densities of the states overlap, the charge transfer occurs.

FIG. 12a shows one or more nanostructure sensing elements (1201) and (1201) directly connected to the amplifier (1203) and electronics, which registers the electrical signal. FIG. 12b presents design where the nanostructure sensing elements (1204, 1205, and 1206) are placed between electrodes (1207), which are connected to the amplifier.

FIG. 22a presents a sample device (2201) with the metallic microstrips (2204) on Si substrate (2202) and nanostructures, semiconductors quantum dots (2203) placed between the microstrips (2204). The microstrips are separated for 50 microns, see FIG. 22b, and each of the microstrips is connected with the golden wires (2205) to the separate channel of presented two VA chips (2206), which are amplifying the signals from microstrips and also provide bias for the micro strips and nanostructures. The chips also allow external triggering and timing with the other equipment and external electronics and are further connected with the data acquisition system through the wires (2207). The connector (2208) connects the device (2201) with a computer. FIG. 22c is Atomic Force Microscope image of the quantum dots (2203) placed between microstrips (2204) on Si substrate (2202). Different symbols (circles, triangles, squares, and pentagons) are used for quantum dots (2203) to emphasize that each group of the quantum dots placed between two microstrips has different sizes or shapes and therefore different density of states.

DETAILED DESCRIPTION OF THE INVENTION

The method will be described by giving the examples. The invention includes any method in which the quantum confinement is used to design the nanostructures, used in the method, in such way that the energy levels in the nanostructures match the energy levels in the targeted analytes. The current examples are not meant to limit the scope of the invention, and it will be understood that a number of different methods can be implemented utilizing described examples.

Figure 1:
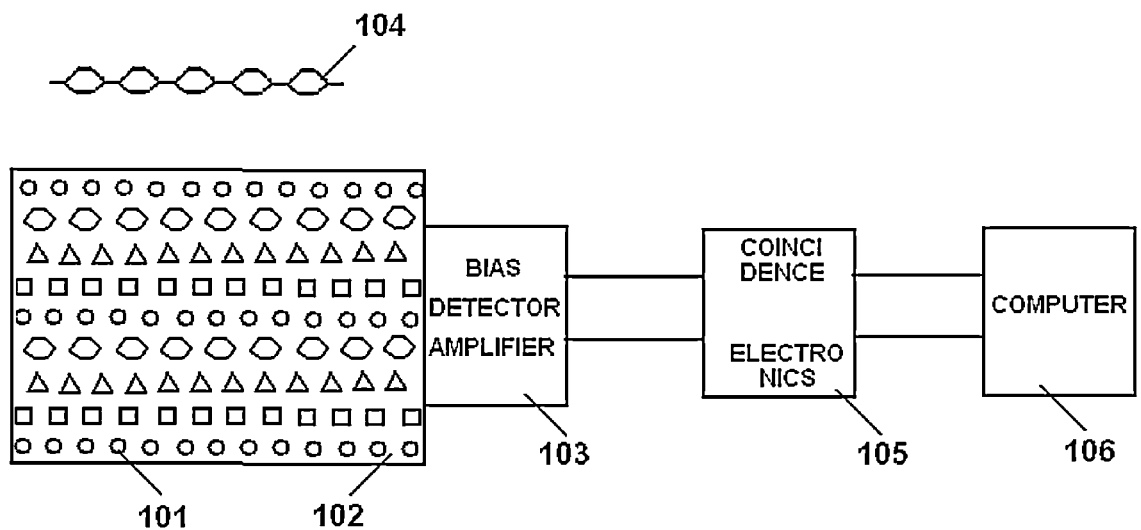
FIG. 1 illustrates a device that is the base for our method. According to the invention wherein a plurality of nanostructures (101) on a substrate (102) is connected to the chip (103) that supplies electrical bias to the nanostructures and also measures the charge and/or energy transfer between an analyte (104) and the nanostructures (101). The chip (103) also amplifies the signal and transmits signal further to the electronics (105), which may include coincidence units, and to the computer (106).

For illustrative purpose only, the invention is embodied in the apparatus shown in FIG. 1. Shown is a plurality of nanostructures (101) on a substrate (102) connected to the chip (103) that supplies electrical bias to the nanostructure and also measures the charge and/or energy transfer between the analyte (104) and the nanostructure (101); or/and the transfer between the nanostructure elements (101). The chip (103) also amplifies the signal and transmits signal further to the electronics (105), which may include coincidence units, and to the computer (106).

Again for illustrative purpose only, we will first give an example of the detection method and then latter we will explain the method in more details. For instance if we would like to detect oxygen and to distinguish if it is in the form of: O, $O_2$, or $O_3$ we can use apparatus described in FIG. 1. For this purpose we will need three different groups of nanostructures (101), for instance three different groups of quantum dots. One group of quantum dots that will have shape, size, and compositions, which will give that group of quantum dots, through quantum confinement, distribution of energy levels (density of states) the same as it is the distribution of the energy levels (density of states) in, for instance, molecule O. The second group of quantum dots (101) will be designed (shape, size, composition) to give this group of quantum dots the same distribution of the energy levels (density of states) as it is in the molecule $O_2$. The third group of quantum dots (101) will be designed to have distribution of energy levels as it is in molecule $O_3$. One will then monitor by electronics (105) charges received in each of these three groups of quantum dots. If, for instance, charges are detected in the quantum dots group number 1, it will mean that a molecule O is present, because only presence of a molecule O can generate charges in the quantum dots group number 1. Other molecules will generate chargers in other quantum dots groups, but not in the quantum dots group number 1. For instance $O_2$, will generate charges only on quantum dots group number 2; and $O_3$ in quantum dots group number 3. This is description of an ideal detector. In reality it is hard to mimic all energy levels in an analyte with just one quantum dot. To detect one molecule, one analyte, in general we will need to have several quantum dots, a group of quantum dots, in which each quantum dots will mimic a part of the energy spectrum of the analyte. Only if all quantum dots in that particular group, that mimic that molecule, will experience charge transfer, only then we can say that that analyte is present. If one of the quantum dots in the group will not be active it means that in the proximity of that group is a similar analyte, but not targeted one. This is underlined in the claim one with wording "plurality of nanostructures". This also demonstrates the mechanism that will give our method high selectivity. The high sensitivity of our method is also ensured, because the quantum dots are designed to have maximal overlap of the energy levels with the analyte, which will result in the highest tunneling of charges between analyte and quantum dots, higher than in the systems that are not designed on this way.

The present invention provides new method, based on new generation of biochemical sensors, for sensitive detection of target analytes. The sensor is based on the principles of quantum confinement, applied on the nanostructures. The term "nanostructure" includes and it is applied to: superlattices, quantum dots, quantum wires, nanotubes, thin films, nanopores and other objects with size depended properties (e.g. electrical, chemical, and optical properties). Quantum dots can be differentiated from a quantum wire and quantum well, which have size dependent properties along at most one and two dimensions, respectively. Nanostructures can exist in a variety of shapes, including but not limited to cylinders, spheroids, tubes, rods, discs, pyramids, rings, and a plurality of other geometric and non geometric shapes.

The quantum confinement effect occurs when electron and hole pairs are spatially confined within the nanostructure. When the size of a nanostructure is on the level of a hundred nanometers or less the confinement breaks the periodic potential, and thereby collapses the energy "bands" into separated energy levels. The energy level distribution in such nanostructures becomes discontinuous, since the charges cannot obtain arbitrary energy values but rather only discrete ones. The energy level distribution and other material properties in such nanostructures depend, among other factors, on the size and the shape of the nanostructures.

Density of states: Each nanostructure, such as quantum dots has discrete distribution of the energy levels. Also each analyte, such as for instance a molecule $O_2$ also has discrete energy levels. There is a probability of occupying energy level in quantum dots (some energy levels may be not occupied); in a molecule all energy levels are occupied. The distribution of density of states is distribution of the energy levels multiplied by the probability that energy level is occupied by an electron.

Figure 2:
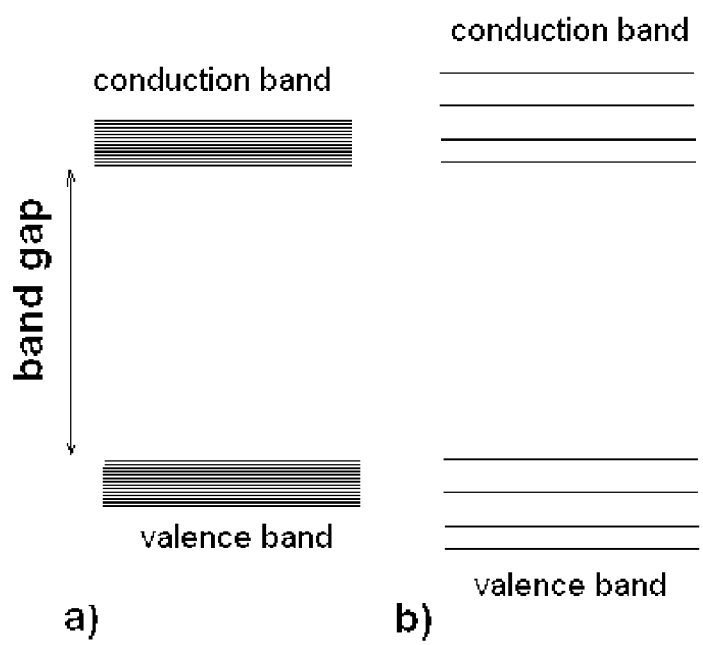
FIG. 2a illustrates energy level distribution in a bulk material.
FIG. 2b illustrates energy level distribution in a nanostructure whit a strong confinement. One can see continuous distribution of energy levels in bulk material and discrete energy level distribution in nanostructures.

FIG. 2a illustrates the energy level distribution in a bulk material and FIG. 2b illustrates the energy level distribution in a nanostructure with a strong confinement. One can see continuous distribution of energy levels in a bulk material and discrete energy level distribution in a nanostructure.

The analyte or targeted analyte may be any or plurality of chemical elements, compounds, molecules, bio molecules, bio agents, nucleotides, genes, nucleic acids (natural or synthetic), viral RNA and DNA, bacterial DNA, fungal DNA, cDNA, mRNA, DNA and RMA fragments, PNA (peptide nucleic acid), DNA (both genomics and cDNA), RNA or hybrid (where the nucleic acid contains any combination of deoxyribo and ribo nucleotides, and any combinations of bases), single base pairs of DNA and RNA, proteins, various toxins, fungi, parasites, *rickettsia*, microbial cultures, viruses, bacteria, or uniquely identifiable components of byproducts, oligonucleotides, etc.

The detection methods and potential applications include, but are not limited to: chemical, biochemical or biological analysis, process control, diagnosis, monitoring of diseases, DNA sequencing, chemical and biocatalysis, bioseparation, synthesis, immobilization of the biological and/or chemical agent, binding, isolating and concentrating the biological and/or chemical agents as well as maintaining the agent structure, activity and stability, etc.

Figure 3:
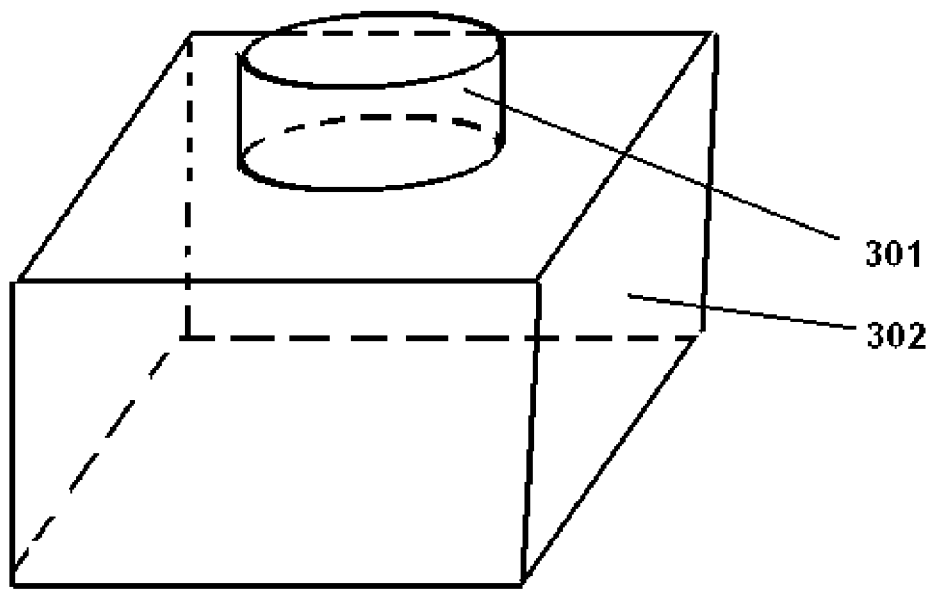
FIGS. 3a and 3b are a schematic of an individual quantum dot (301) on a substrate (302), or quantum dot (303) in a substrate (304).
Figure 3:
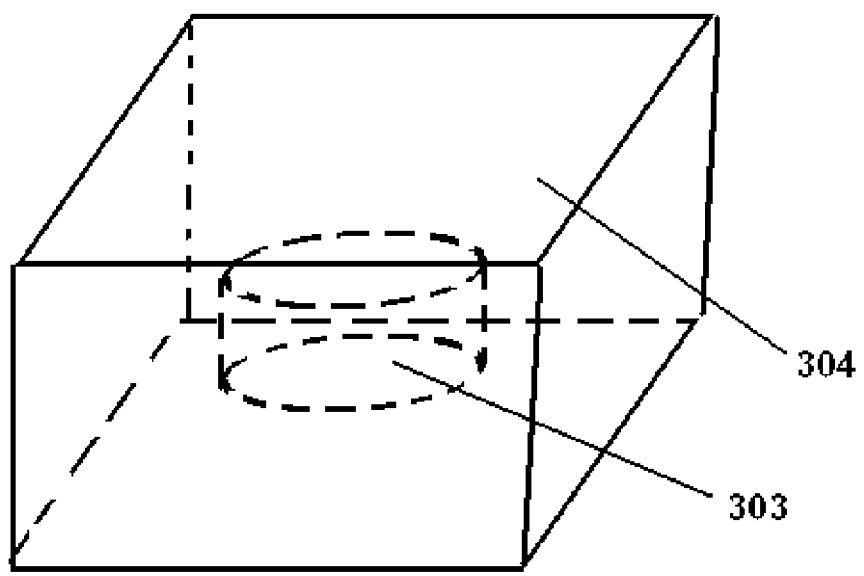

FIG. 3a and FIG. 3b are a schematic of an individual quantum dot (301) on a substrate (302) or quantum dot (303) in a substrate (304). For example, the quantum dot may be made from an island (301) or insertion (303) of narrow-band-gap material on a wide-band-gap substrate (302) or (304). If such islands or insertions are large enough, they may be considered as locally formed quantum well (QW) insertions. If, on the other hand, the lateral size of the islands is comparable with or smaller than the excitonic Bohr radius and the band-gap difference between the island and the substrate material is large enough, quantum dots (QDs) are formed. They are confined in all three dimensions: one dimension of the confinement is defined by the QW width; the other two lateral dimensions are defined by the effective size of the QD island. While the vertical confinement is always strong, the lateral confinement may be both strong and weak, depending on a particular physical properties of the substrate and deposit, and a specific growth conditions. V. A. Schukin, N. N. Ledenbsov, D. Bimberg, Epitaxy of Nanostructures, Berlin, Springer 2004.

Figure 4:
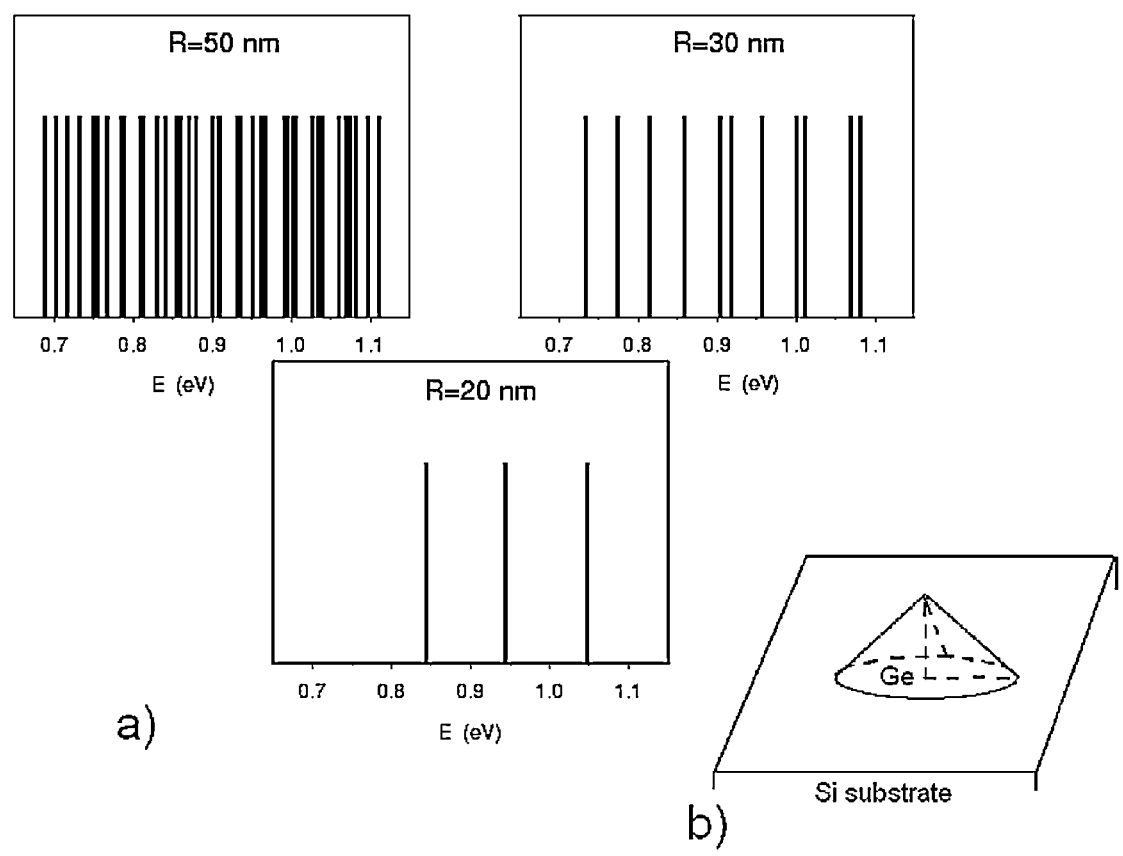
FIG. 4 shows the energy levels for cylindrical quantum dots Ge on Si substrate as a function of size of the quantum dots. The energy levels for the radial sizes of 20, 30, and 50 nm are shown.

The energy level distribution in the nanostructure as a function of the size of the nanostructure is illustrated in FIG. 4 for the case of the cylindrical Ge quantum dots on Si substrate. To get these results one needs to solve the Schrödinger equation. In this example, inputs into Schrödinger equation include potentials that take into account stress between the quantum dots and substrate, the material composition, and also the difference in the energy gap of the quantum dot and substrate. The figure demonstrates that by reducing the radius of the quantum dots the ground state energy level moves toward the higher energies and the entire spectrum also changes. B. Vlahovic, I. Filikhin, V. M. Suslov and K. Wang, Numerical Simulation of Electronic Properties in Quantum Dot Heterostructures. Technical Proceedings of the 2004 NSTI Nanotechnology Conference and Trade Show, Vol. 3, pp 130-132; I. Filikhin, E. Deyneka and B. Vlahovic, Single electron levels of InAs/GaAs quantum dot: comparison with capacitance spectroscopy, Physica E 31 (2006) 99; I. Filikhin, V. M. Suslov and B. Vlahovic, Modelling of InAs/GaAs quantum ring capacitance spectroscopy in the non parabolic approximation, Phys. Rev. B 73 (2006) 205332; I. Filikhin, E. Deyneka and B. Vlahovic, Modeling of InAs/GaAs self assembled heterostructures: quantum dot to quantum ring transformation, Journal of Vacuum Science & Technology A: Vacuum, Surfaces, and Films, 24 (2006) 1249; I. Filikhin, V. M. Suslov, M. Wu and B. Vlahovic, Effective approach for strained InAs/GaAs quantum structures, Physica E 40, 715 (2008); I. Filikhin, V. M. Suslov, M. Wu and B. Vlahovic, InGaAs/GaAs quantum dots within an effective approach, Physica E 41, 1358-1363 (2009); I. Filikhin, S. G. Matinyan, B. K. Schmid and B. Vlahovic, Electronic and level statistics properties of Si/SiO$_2$ quantum dots, Physica E 42, 1979-1983 (2010).

Figure 5:
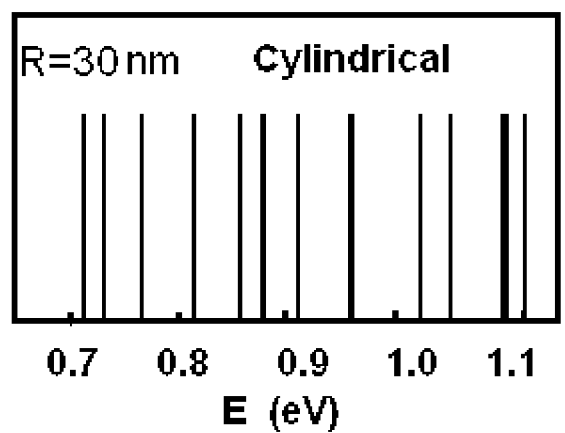
FIG. 5 shows how the energy level distribution of a quantum dot depends on the shape of the quantum dot. The energy levels for the cylindrical, conical, and pyramidal shape quantum dots are presented. The difference in the distribution is significant, even all structures have the same radial size.
Figure 5:
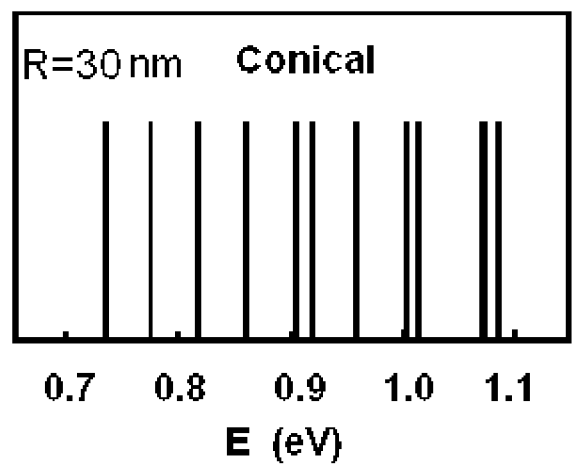
Figure 5:
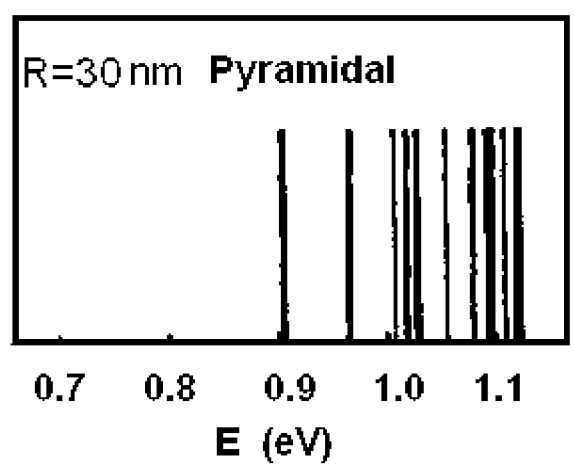

Not only the size, but also the shape of the quantum dots has effect on the energy level distribution in a nanostructure. The nanostructures that have the same volume but differ in shape will in general have different energy states distribution. FIG. 5 shows how the energy levels distribution of a quantum dot depends on the shape of the quantum dots. The energy level distributions for the cylindrical, conical, and pyramidal quantum dots are presented. Again the energy levels are obtained by solving the Schrödinger equation; the input is the stress between quantum dots and substrate, and band gap potentials. See the previous reference, B. Vlahovic et al.

The calculation of the distribution of density of states is complex task, because it depends on size, shape, material composition, stress generated between the nanostructure and substrate, and external factors. These calculations usually require use of supercomputers and significant amount of computer time. However, when properties of material are known, very accurate results with an effective approach can be also obtained, see for instance I. Filikhin, V. M. Suslov, M. Wu and B. Vlahovic, InGaAs/GaAs quantum dots within effective approach Physica E 41, (2009) 1358-1363.

Figure 6A:
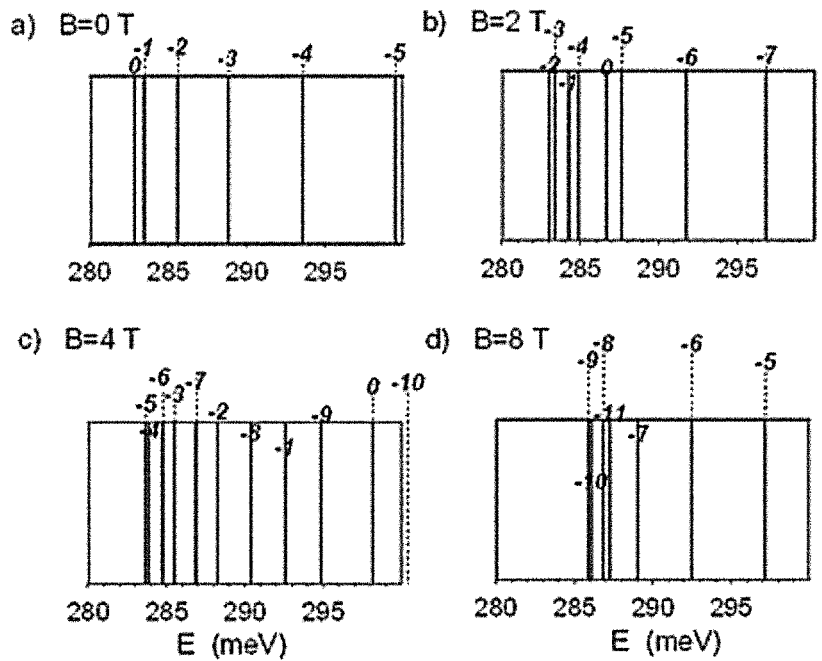
FIG. 6a demonstrates significant changes in the energy level spectrum when the strength of magnetic field changes from B=0 T, B=2 T, B=4 T, to B=8 T.
Figure 6B:
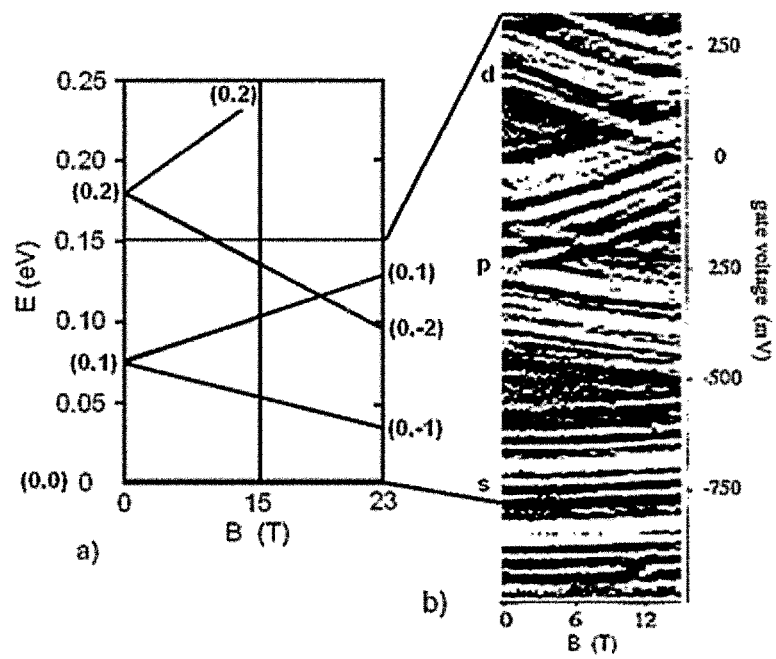
FIG. 6b demonstrates similar energy level dependence on the change of the magnetic field for electrons with two different quantum numbers (0,1) and (0,2).

The external factors, such as externally applied magnetic field, electrical bias, temperature, and pressure, may significantly change the distribution of density of states. FIG. 6 shows the change of the electron energy levels inside quantum ring, FIG. 6a, and cylindrical shape quantum dots FIG. 6b, when the external magnetic field is applied. The obtained values are again the solutions of the Schrödinger equation when the band gap and external magnetic fields are used as the inputs for the potential. FIG. 6a demonstrates the shift of the electron energy levels caused by the external magnetic field for InAs quantum ring embedded in GaAs substrate, with the inner radius $R_1$=10 nm, the height H=1.5 nm and the outer radius $R_2$=40 nm.

FIG. 6b shows calculation of electron excitation energy levels for InAs/GaAs cylindrical shape (H=7 nm and R=10 nm) quantum dot for different values of the magnetic field strength B from 0 to 23 T. One can see excellent agreement between the calculations and the experiment, the gray-scale plot of the capacitance-gate voltage experimental traces that corresponds to the electron energy states. The quantum numbers of the electron states are marked as (n; l), where n is radial quantum number and l is orbital quantum number. The first line (0,0) of the plot corresponds to an occupation of the ground state (s-state) level of an electron pair with different projections of spins. The next double line (0,1) corresponds to an occupation of the p-state. The d-state represents the last double lines (0,2). The double lines, two lines for each state, is manifestation of the angular Zeeman-splitting, which lids to departing lines corresponding to the states with non-zero angular momentum. The broadening of the lines to the stripe is due to the variation of the size of quantum dots during the fabrication. The calculations for FIG. 6a are from I. Filikhin, V. M. Suslov and B. Vlahovic, electron spectral properties of the InAs/GaAs quantum ring, submitted to International journal of Nanoscience (2005). The reference for calculations of FIG. 6b is I. Filikhin, E. Deyneka and B. Vlahovic, Energy of electron states of InAs/GaAs quantum dot, submitted to Appl. Phys. Lett. (2005). The experimental results are from B. T. Miller, W. Hansen, S. Manus, R. J. Luyken, A. Lorke, and J. P. Kotthaus, S. Huant, G. Medeiros-Ribeiro and P. M. Petroff, Phys. Rev. B 56, 6764 (1997).

Consequently, in the design of the detector based on the quantum confinement, one needs to perform similar calculations. If the bias voltage or/and external electromagnetic field, magnetic field, and the temperature are applied, then one also needs to take these factors into consideration.

Figure 7:
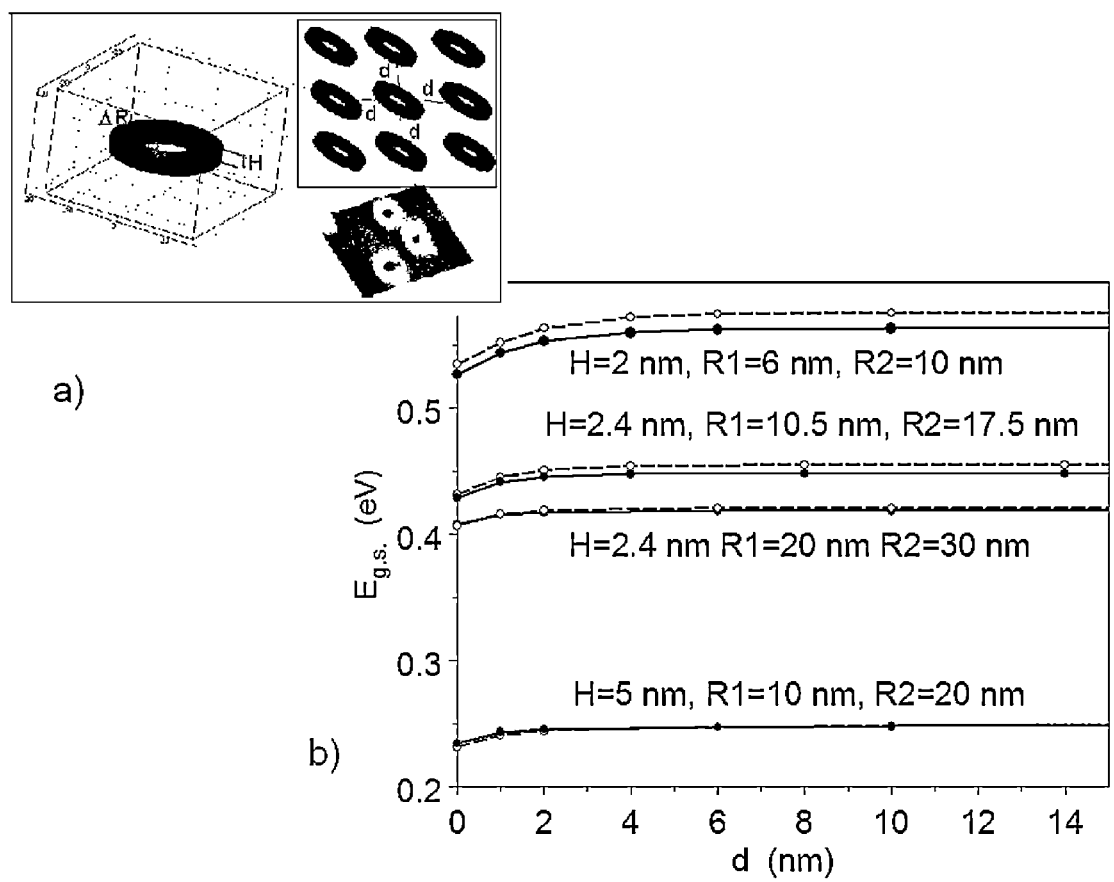
FIG. 7 shows the impact of the collective effects of the array of quantum dots, for the quantum dots in a form of a quantum ring. The ground energy state of a quantum ring will be affected by the presence of other quantum rings. When the distances between the quantum rings are large, the energy level distribution in a quantum ring is the same as if the quantum ring was alone, isolated from other quantum dots. When the distances between the quantum rings are small, the collective effect of the array of quantum rings shifts the energy levels inside rings toward lower value.

It is necessary to mention that the energy levels in a single nanostructure will be different when that nanostructure is isolated from other nanostructures, then when that nanostructure is a part of two dimensional arrays of nanostructures or three dimensional arrangements of nanostructures. The impact of these collective effects to the energy levels is demonstrated in FIG. 7. Shown are the electron ground states inside a quantum ring as a function of the distances between the rings. When the separation is large, the energy levels in the quantum ring are the same as when the ring is isolated. When distances between the rings are small, the effects of the array shifts the energy levels in the quantum rings towards lower energy values. One also needs to take this effect into account when engineering the device.

Figure 8A:
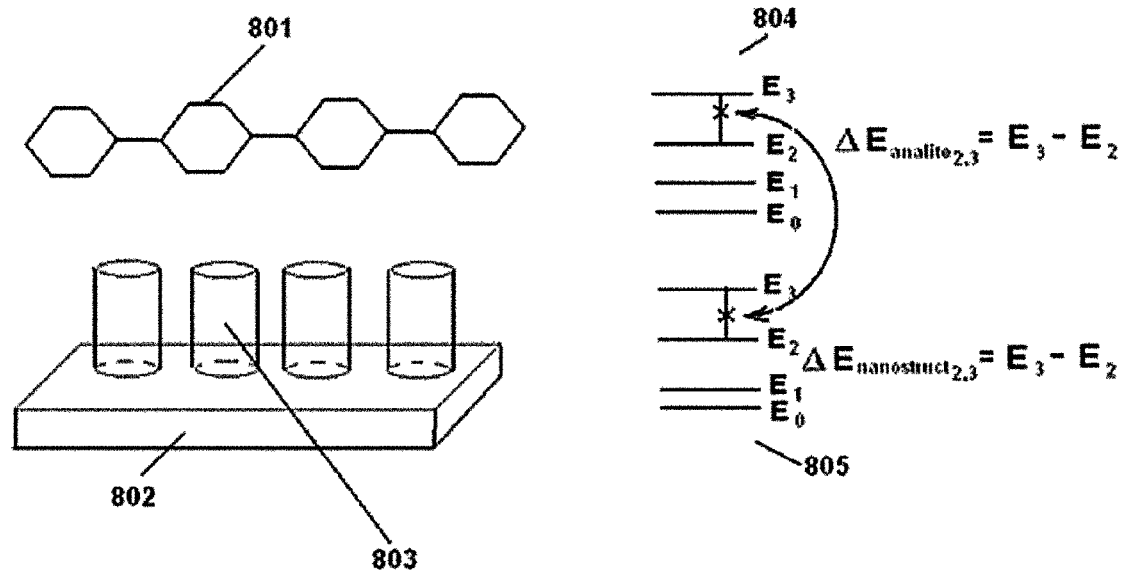
FIG. 8a illustrates the basic principle of the detection method. The charge and/or energy transfer between the detector's (802) nanostructure elements (803) and the targeted analyte (801) will happen only if the density distribution of the energy levels of the nanostructure (805) overlaps with the density distribution of the energy levels of the analyte (804).
Figure 8B:
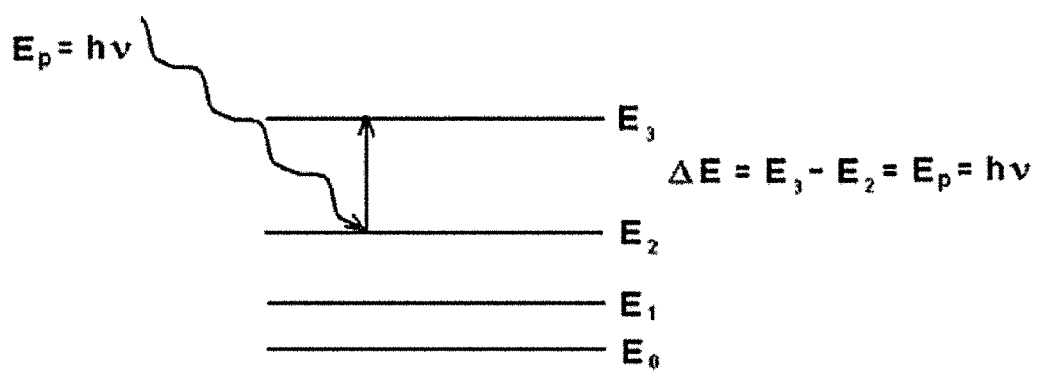
FIG. 8b illustrates analogy with the optical spectroscopy, where a photon will be absorbed by the material only if the energy levels inside material correspond to the photon energy.

The basic principle of the method is that the charge or/and energy transfer between the detector nanostructure elements and the targeted analyte will be proportional to the overlap of the energy level density distribution of the nanostructure and the energy level density distribution of the analyte. The FIG. 8a demonstrates an analyte (801) above a nanostructure array of quantum dots (803) deposited on a substrate (802). In this example, the density of states for the analyte (804) are the same as the density of states for the quantum dots (805), which will make the charge and/or energy transfer between the analyte and the quantum dot possible. The situation is the same as in the optical spectroscopy, where a photon will be absorbed by material only if the energy levels inside material correspond to the photon energy, as it is demonstrated in FIG. 8b.

Figure 8C:
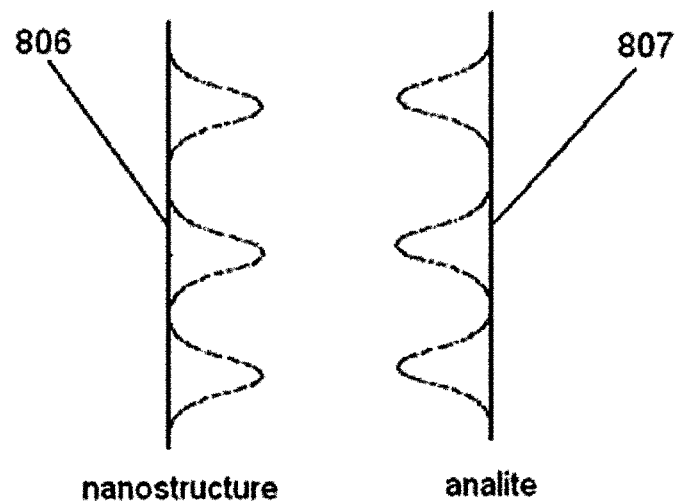
FIGS. 8c and 8d demonstrate charge and/or energy transfer as a function of the overlap between the densities of the states.
Figure 8D:
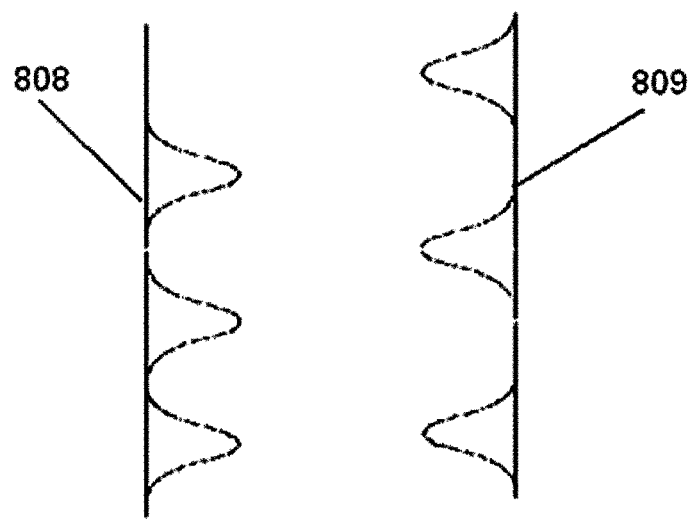

This is the most important part for the operation of the device, so for that reason additional view of the same situation is given in FIG. 8c. The density of states for a nanostructure are denoted by 806, and those for an analyte by 807. Since the densities of states are identical, the charge transfer between the nanostructure and the analyte will occur when an electrical bias is applied on the nanostructure. In the case where the analyte and the nanostructure have different densities of states, as shown in FIG. 8d where there is no overlap between the nanostructure density of states (808) and the analyte density of states (809), the charge transfer between the analyte and the nanostructure will not be possible, regardless of the electrical bias applied on the nanostructure.

Figure 8E:
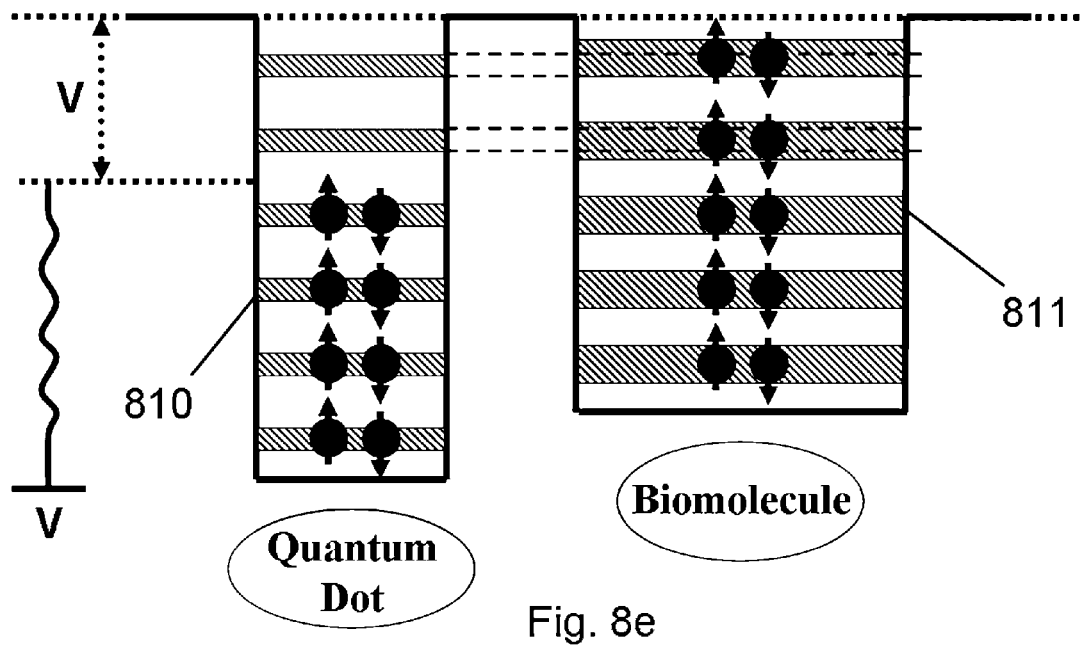
FIG. 8e presents the overlap between the density of the states of the quantum dot (810) and analyte (811), which results in the charge transfer between the analyte and quantum dots.
Figure 8F:
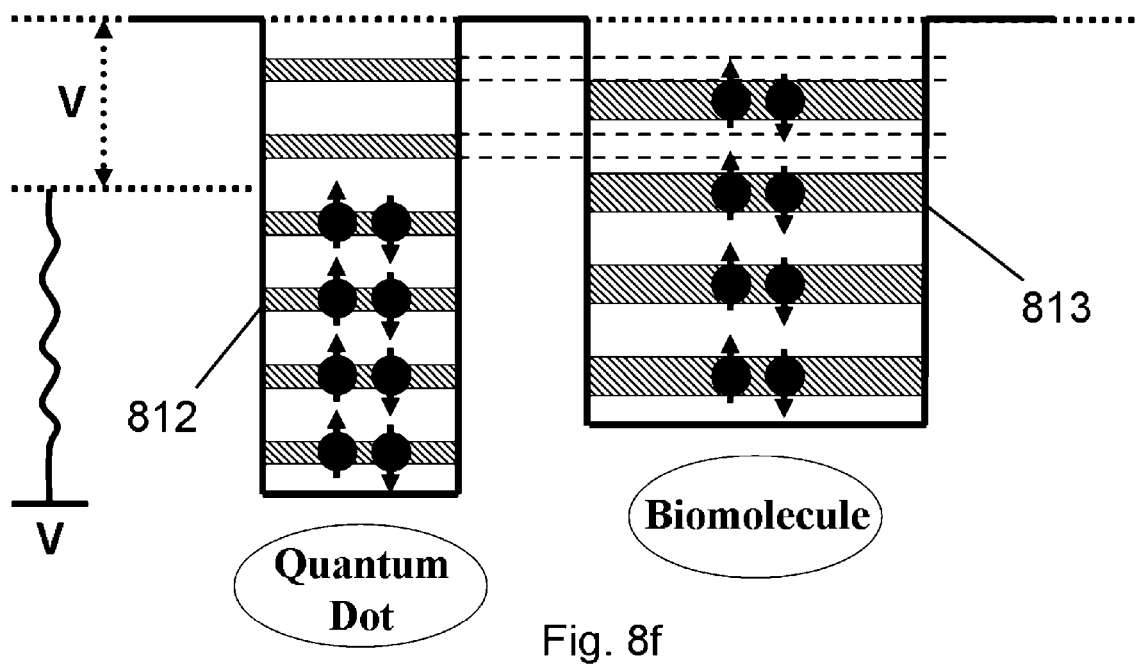
FIG. 8f shows the density of states of nanostructure (812) that has no overlap with the density of states of an analyte (813); in this example there will be no charge tunneling/transfer between the nanostructure and analyte.

One more detailed description of the detection mechanism is shown in FIG. 8e. Here the nanostructure density of states (810) is represented by the electronic confinement levels shown as (810). The levels are broadened due to various energy/momentum relaxation mechanisms. The figure demonstrates the case where the lower energy levels are occupied but some upper energy states are free, for instance due to the electrical bias applied. The analyte (biomolecule) density of states is represented by (811), and in this example all molecular energy levels are shown as occupied and broadened due to electron relaxation effects. Now, when there is overlap between the density of states of the nanostructure and analyte, as in the example shown, the charge tunneling from the molecule to the analyte will occur. If there is no overlap of the density of states, the tunneling from the molecule to the analyte will not occur. For instance, FIG. 8f shows the density of the states of nanostructure (812) that has no overlap with the density of states of an analyte (813); in this example there will be no charge tunneling transfer between the nanostructure and the analyte.

Figure 9:
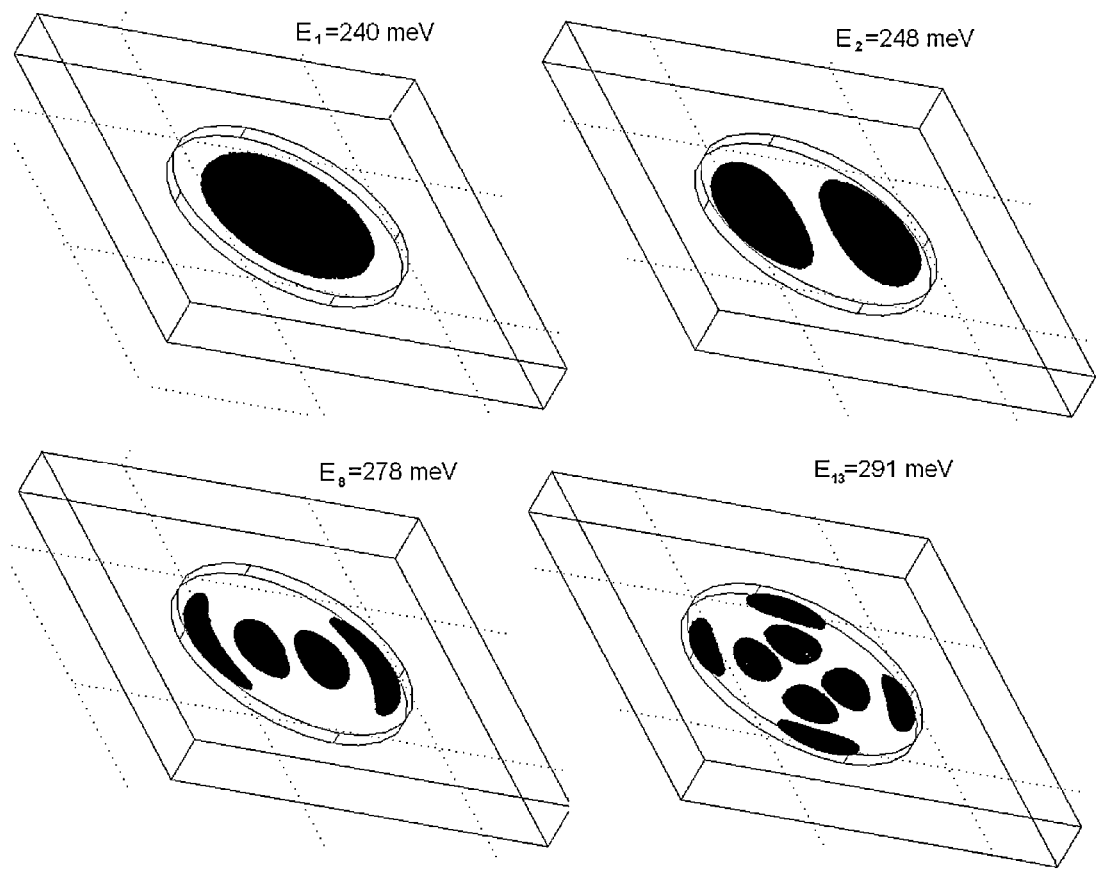
FIG. 9 shows square wave functions for cylindrical quantum dot; the figures correspond to the ground state l=0, and to the exited states (n=1, l=1), (n=1, l=2), and (n=1, l=4) respectively.

The density of states of the nanostructure and analyte can be obtained from the spectrum of the eigenstates by evaluation of the corresponding integrals which include the nanostructure and analyte wave functions. The wave functions are obtained also as solutions of the Schrödinger equation. As an example, FIG. 9 shows square wave functions for cylindrical quantum dot; the figures correspond to the ground state l=0, and to the exited states (n=1, l=1), (n=1, l=2), and (n=1, l=4) respectively.

The distribution of the density of states will depend on the effects of size, strain, composition, applied magnetic fields, applied electrical bias, applied electromagnetic fields, temperature, collective effects, and other parameters. The amount of the charge and/or energy transport between the elements of detector nanostructure and the targeted analyte will be proportional to the overlap between the density of states of the nanostructure and the density of states of the targeted analyte. Johnson et al. calculated the electronic and transport properties in $Si_xGe_{1-x}$ quantum wires and quantum dots with finite element modeling; T. Johnson, L. B. Freund, C. D. Akyüz, and A. Zaslaysky, Finite element analysis of strain effects on electronic and transport properties in quantum dots and wires, *J. Appl. Phys.*, 84, 3714-3725 (1998). Their calculations were consistent with the experimental results. For example, see M.-E. Pistol, N. Carlsson, C. Persson, W. Seifert, and L. Samuelson, Observation of Strain Effects in Semiconductor Dots Depending On Cap Layer Thickness, *Appl. Phys. Lett.* 67(10), 1438 (1995); C. D. Akyuz, A. Zaslaysky, L. B. Freund, D. A. Syphers, and T. O. Sedgwick, Inhomogeneous strain in individual quantum dots probed by transport measurements, *Appl. Phys. Lett.* 72(14), 1739-1741 (1998). See also I. Filikhin, E. Deyneka and B. Vlahovic, Energy dependent effective mass model of InAs/GaAs quantum ring, Modelling Simul. Mater. Sci. Eng. 12, 1121-1130 (2004).

Figure 10:
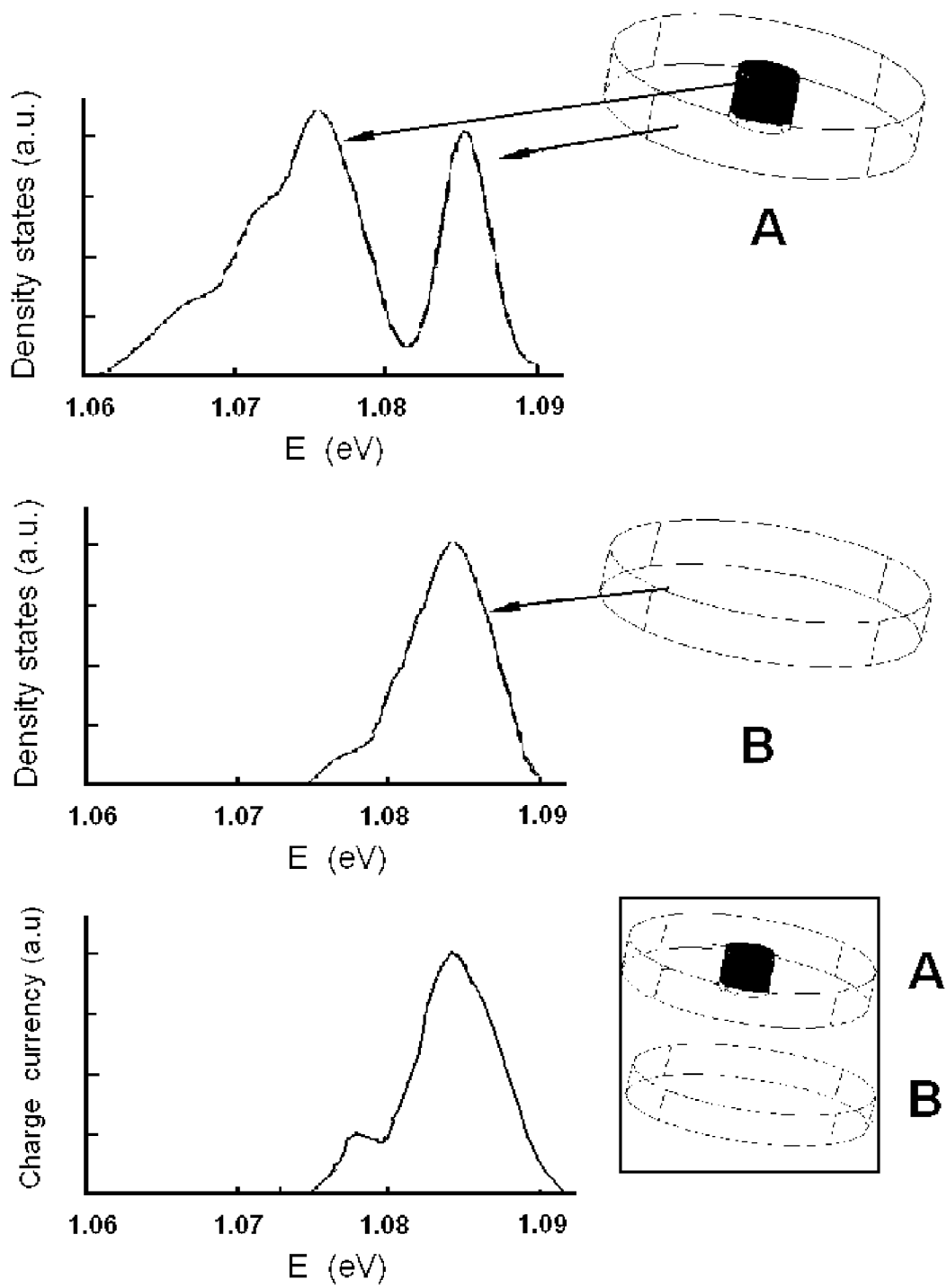
FIG. 10 demonstrates the charge transfer as a function of the overlap between the densities of states. The density of states for an inhomogeneous quantum dot are presented on the figure at the top of the page, the density of states for a homogenous quantum dot are presented on the figure below. The charge transfer between these two structures will be proportional to the overlap of the density of states as it is shown on the lower figure.

FIG. 10 demonstrates the charge transfer as a function of the overlap between the densities of states. The A denotes a composite quantum dot which has the first peak of the density states that corresponds to the inner part of the quantum dot, and the second peak of the density of states that corresponds to the outside part of the quantum dot. The B represents a homogeneous quantum dot with its density of states. When two quantum dots A and B are placed together (AB), and a bias is applied, the charge transport between the quantum dots occurs. One can see that the amount of the charge transport is proportional to the overlap between the density of states for quantum dot A and quantum dot B.

Figure 11:
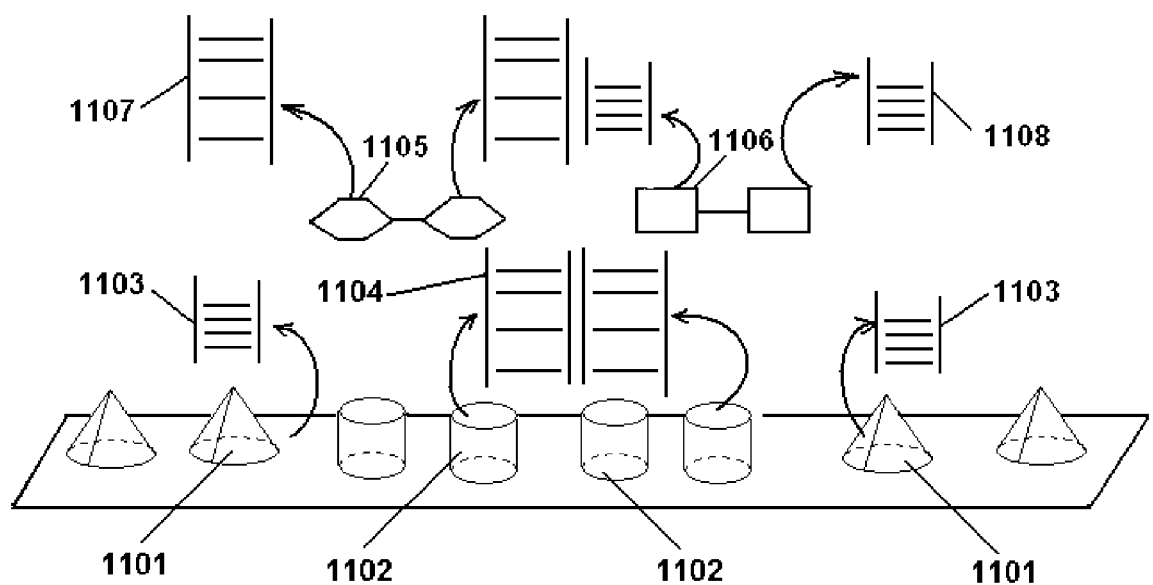
FIG. 11 demonstrates application of the quantum confinement when the method is applied for detection of analytes represented as (1105) and (1106). In case where the density-of-states distributions (1103, 1104) in the sensing nanostructures (1101, 1102) overlap with the density-of-states distributions (1107, 1108) in the targeted analytes (1105, 1106), the charge and/or energy transfer will occur. For instance It will occur between nanostructure (1102) and analyte (1105), because the energy distributions (1104) and (1107) are the same. When the density distributions of the energy levels in the sensing element and the analyte are different, as for instance in analyte (1106) and nanostructure (1102), there will be no charge transfer between the analyte and nanostructure.

The application of the quantum confinement in the biochemical detector is demonstrated in FIG. 11. The nanostructure sensing elements (1101) and (1102) are built with the specific energy levels and specific energy states distributions (1103) and (1104), respectively. Above the sensing element shown are the targeted analytes (1105) and (1106), with their density-of-states distributions (1107) and (1108), respectively. In the case where the density-of-states distribution in the sensing nanostructure is the same as in the targeted analyte, the charge and/or energy transfer will occur. This is the case where the analyte (1105) is over the nanostructure (1102), since the density of states (1107) of the analyte (1105), is the same as the density of states (1104) of the nanostructure (1102). This is also the case when the analyte (1106) is over the nanostructure (1101), since the density of states (1108) and (1103) are the same. In both cases there will be the charge transfer from the analyte to the nanostructure, when an electrical bias is applied on the nanostructure. When the density of states in the sensing element and the analyte are different, the density of states (1107) of the analyte (1105) and the density of states (1103) of the nanostructure (1101), and also the density of states (1108) of the analyte (1106) and the density of states (1104) of the nanostructure (1102), there will be no charge transfer.

Figure 12A:
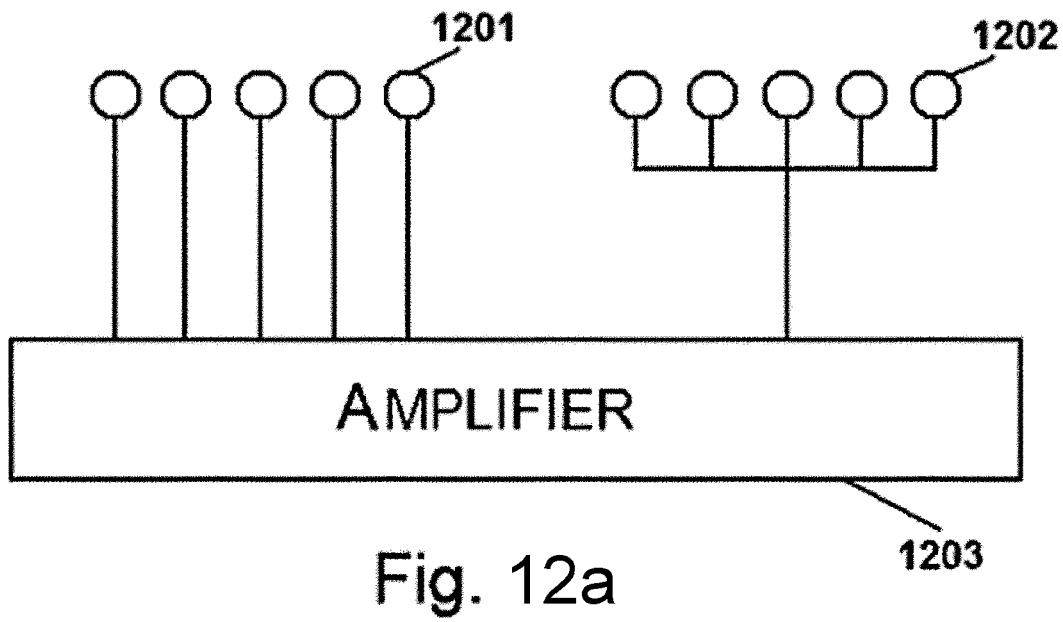
FIGS. 12a and 12b are the two schematics of a possible design of the detection system.
Figure 12B:
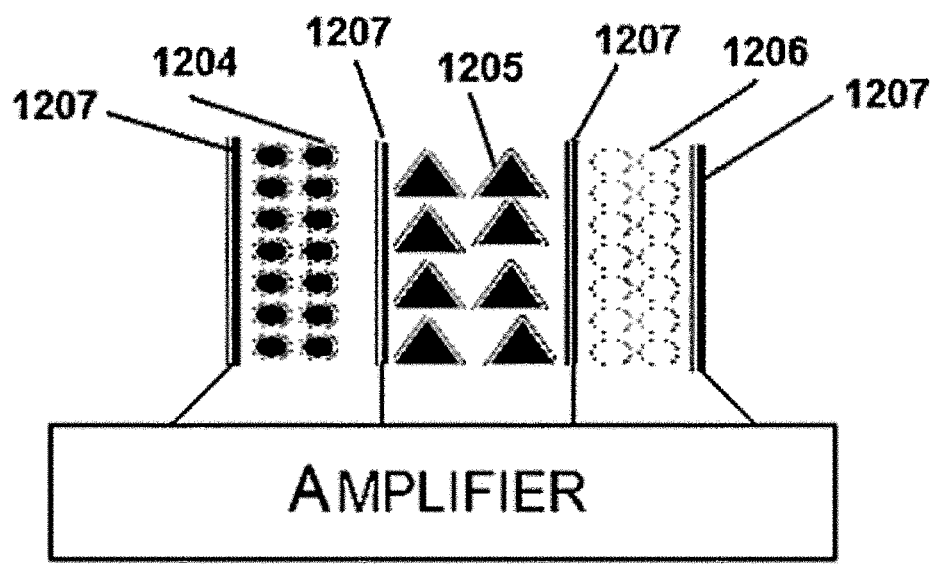

Two schematics of the possible design of the detection system are presented in FIGS. 12a and 12b. FIG. 12a shows one or more nanostructure sensing elements (1201) and (1202) directly connected to the amplifier (1203) and electronics, which registers the electrical signal. FIG. 12b presents designs where the nanostructure sensing elements (1204), (1205) and (1206) are placed between electrodes (1207). When the charge and/or energy transfer between the nanostructure sensing elements and the analyte occurs, the electronics registers charge transfer, current, change of conductivity, capacitance, impedance, or change in any other electrical property, associated by the electrodes and nanostructures.

Figure 13:
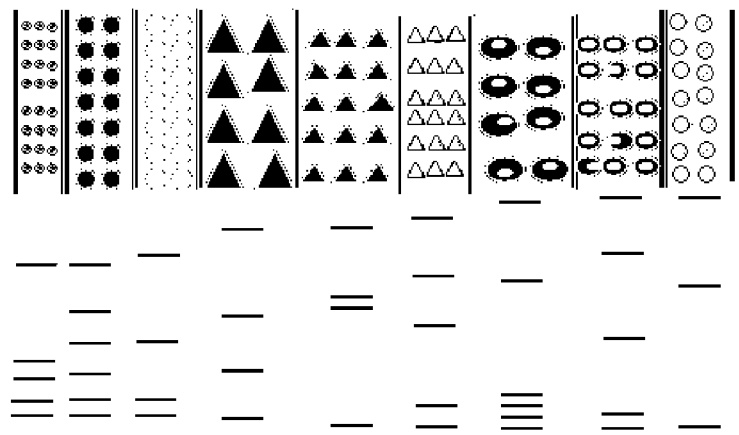
FIG. 13, a part at the top of the page, presents arrays that contain segments with different nanostructures and varying spacing between them. Each segment of the array is designed to detect different analyte or a part of the analyte with corresponding charge distribution. The lower part of the figure represents the distributions of the energy levels that correspond to the nanostructure arrays presented above.

The nanostructure sensing elements may form an array which can be built for detecting just one specific analyte or may be built for the simultaneous detection of many targeted analytes. The array may contain the nanostructure elements of different shape, composition or spacing. All segments of the array may be the same or each segment of the array can be different. FIG. 13 presents an array that contains several segments with different nanostructures and varying spacing between them. Each segment of the array is designed to detect different analyte or part of the analyte with different charge distribution. The density of states of each part of the nanostructure arrays are denoted below the array. Each part of the array has nanostructures that have different density states, because of that, each part of the array will have charge transfer with the different analytes.

It is important to mention, even it is obvious to someone skilled in the field, that it is hard and in some cases impossible to design single nanostructure, for instance quantum dot, that will have the same density of state distribution as a targeted analyte. For that reason sever in most cases several nanostructures, for instance several quantum dots will be needed to simulate the density of states in the analyte. Each group of the nanostructures will be responsible for a part of the density of states spectrum. In these cases the analyte will be recognized only if the charge and/or energy transfer will be detected for all groups of nanostructures created to simulate analyte. For instance on FIG. 13, each array can be designed to simulate a part of the spectrum and only if signal will be received from all arrays, only than the analyte will be recognized. Some calibration, about the level of the signal that is required for each group of nanostructures to recognize the analyte may be needed. It may be done by testing the device with the known analyte and measuring the signal as the function of the analyte concentration.

Figure 14:
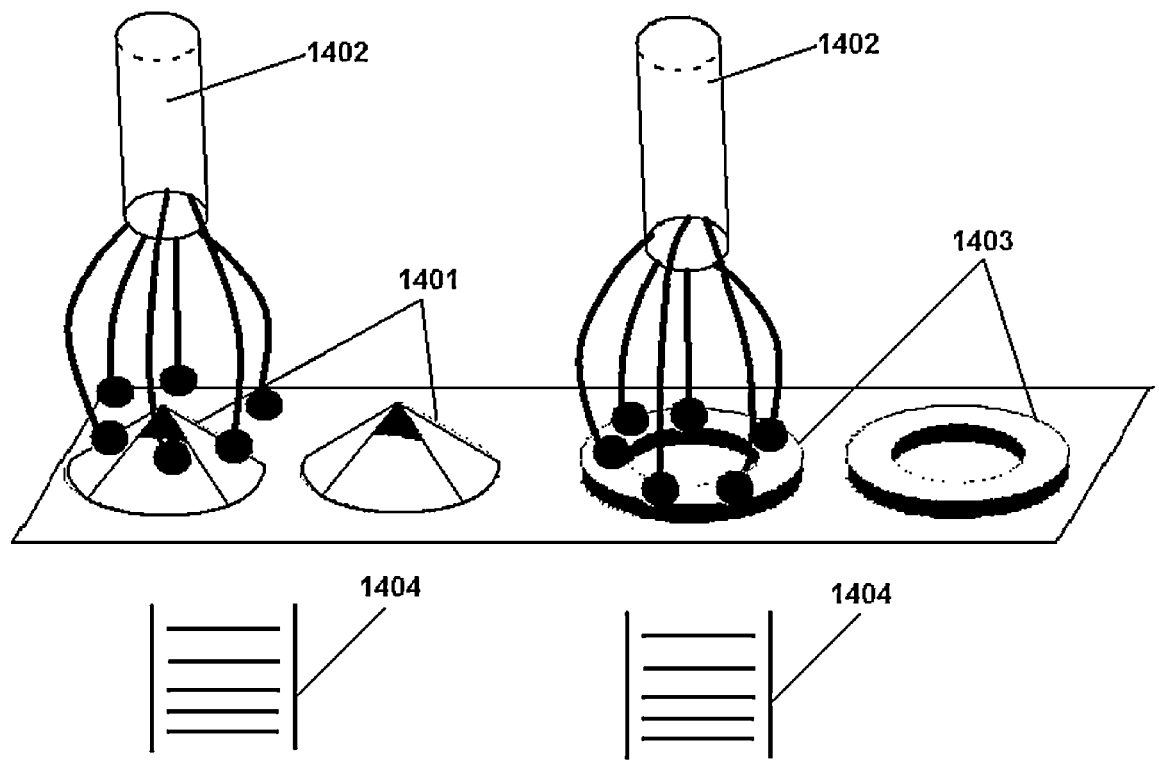
FIG. 14 presents the nanostructures or arrays of nanostructures built with nanostructures (1401, 1403) designed to distinguish between the analytes (1402) that have the same density-of-states distributions (1404) but have different shape or structures. Figure represents the situation where the pyramidal nanostructure will not be able to connect with all of the charge elements of the analyte as well as the ring shape nanostructure.

It is important to note that the nanostructure may be built in such a way to have different shape but the same density-of-states distribution (1404). The arrays built with this kind of nanostructures will be used to distinguish between the analytes which have the same density-of-states distributions (1404) but have different structures. FIG. 14 represents that situation, where the pyramidal nanostructure (1401) will obviously not be able to connect with all of the charge elements of the analyte (1402) as well as the ring shape nanostructure (1403).

Figure 15A:
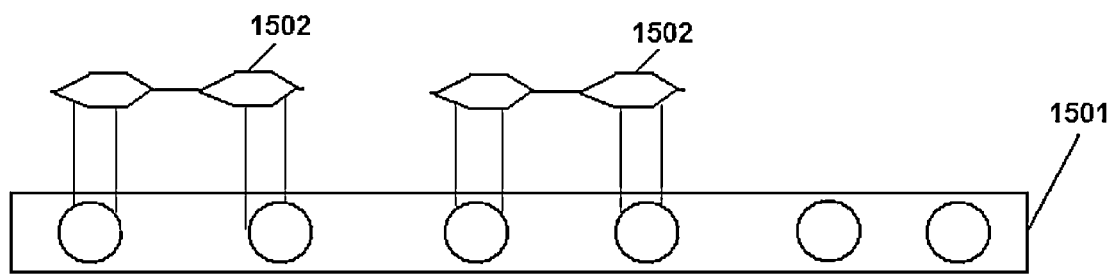
FIGS. 15a and 15b demonstrate importance of the spacing between the nanostructures deposited on substrate (1501). For instance, when the size of the spacing between the nanostructures is comparable to the size of the analyte, both groups of the charges of the analyte (1502) will be detected, FIG. 15a. Only one group will be detected due to the mismatch of the sizes between the analyte and the nanostructure, FIG. 15b.
Figure 15B:
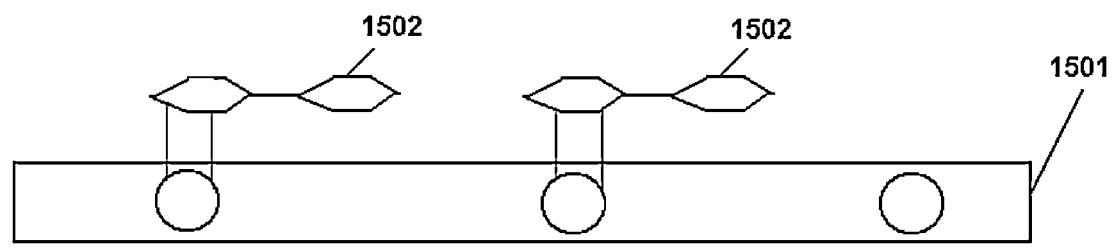

The spacing between the nanostructures is also an important factor, as it is demonstrated in FIGS. 15a and 15b. As the example shown in FIG. 15a demonstrates, when the size of the spacing between the nanostructures (1501) is comparable to the size of the analyte (1502), both groups of the charges on the analyte (1502) will be detected. FIG. 15b shows the situation where only one group will be detected due to the mismatch of the sizes between the analyte and the nanostructure.

The nanostructures can be built from a single homogeneous monoatomic materials or polyatomic materials. The material may be without impurities, or can contain impurities, can be doped or implanted, can be defect free or can contain a range of defects, vacancies, dislocations, etc. The nanostructure can optionally be surrounded partially or completely by another material. Further, we will call a "core" the inner part of the material. The outside or surrounding material we will call a "shell", even when it does not have shell type geometry. For instance, in the case of the quantum dots we can have a "core" as the inner part and a "shell" as the surrounding material. There can be several layers of shells, which can be complete or partially complete.

When nanostructure is for example a nanotube, the nanotube may include inner part, which can be optionally surrounded with one or more layers of materials or shells. The different part of the length of a nanotube may be built from different materials and may have different inner and outer diameters, which are chosen such that quantum confinement provides a desired energy level distribution inside the nanotube.

Thin films and superlattices may also be homogenous, partially homogeneous or substantially inhomogeneous. One layer of the superlattice or thin film may contain areas built from different materials of different thickness to achieve quantum confinement and different state density distributions for different areas or volumes of superlattice or thin film nanostructure based detector.

Nanostructures with or without shell may also be optionally functionalized or hybridized, in order to attract or repel the specific analyte. For instance, they can consist of ligands which can comprise single analyte specie or two or more types of analyte species. The ligands, which are chosen here just as an example, can be one or more active groups or antibodies of particular species of interest for trapping the particular biological agent (antigen). In addition, ligands can be hydrophilic, hydrophobic, or amphiphilic and can be in form of layers, rods, tubes, etc. The ligands can also be oligonucleotides, having for instance a sequence complementary to the sequence of one of the portions of the selected nucleic acid. The "shell" can also be any molecule, molecular group, or functional group coupled (attached) to the nanostructure to impact interaction between the nanostructure and the surrounding material and/or properties of individual nanostructure. It can control electrical, optical, transport, chemical, physical, geometrical spacing or combination of the properties. For instance, a physically rigid active group bound to the nanostructure can act as a physical inter-particle spacing. As other example, a group covalently bound to the nanostructure may enhance charge transfer between the analyte and nanostructure.

The functionalization of the nanostructure can be done on outer and/or inner surface of the nanostructure. It can be done on core and/or shell of the nanostructure. So, for example, the ligand can be also inner part of the nanostructure, for instance, inner part of the nanotubes. Such methods are known in the art, see for instance U.S. Pat. No. 6,828,432B2 and reference therein.

Let as describe as an example the detection of a DNA by a functionalized nanostructures. In general, different portions of the nucleic acid have different sequences which will be recognized with nanostructures carrying one or more different oligonucleotides, preferably attached to different nanostructures. The first oligonucleotide attached to the first nanostructure, for instance first line of quantum dot, has a sequence complementary to the first portion of a DNA. The second oligonucleotide attached to the second nanostructure (second line of quantum dot) has a sequence complementary to a second portion of the targeted sequence in the DNA, and so on. The different parts of an array with different combinations of the functionalized nanostructures will obviously detect the different sequences of the DNA. Knowing which combinations of the nanostructures are active and which nanostructure detected charge transfer will allow one to make the DNA sequence.

Figure 16:
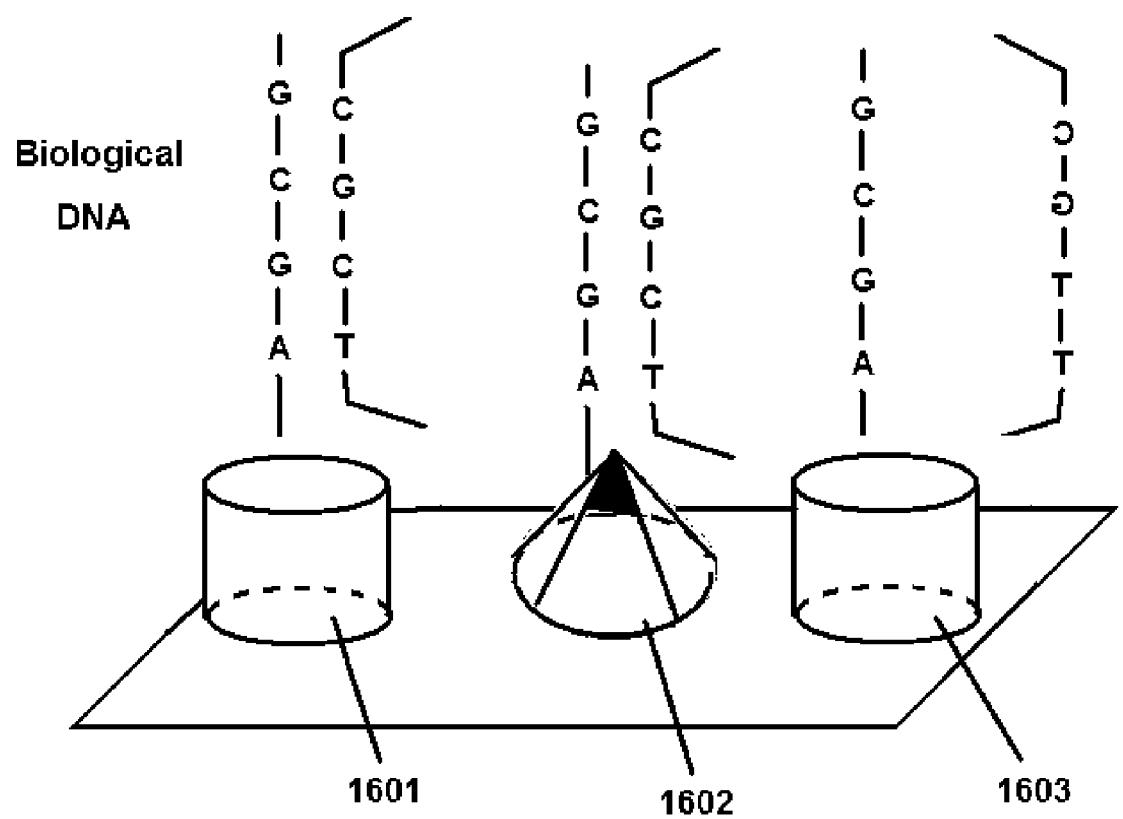
FIG. 16 illustrates importance of the quantum confinement and the density of states and how it gives an additional degree of the selectivity for detection of the species. Quantum dots (1601) and (1602) may have the same functionalization but different density of states. In both cases the complementarity between the DNA and oligonucleotide is satisfied, but the charge transfer between the DNA and the nanostructure will happen only if simultaneously the density-of-states distribution between the nanostructure and the targeted DNA is also matched, for example only between dot (1601) and analyte. There will be no charge tunneling between nanostructure (1603) and analyte, because there that nanostructure is not complementary to the analyte.

Here it is important to mention that the nanostructures (in this example, quantum dots) may have the same functionalization but different density of states, as it is demonstrated in FIG. 16. The first quantum dot (1601) has the same functionalization as the second quantum dot (1602), but the two quantum dots have different energy states. The difference in energy states is illustrated by the different shapes of these two quantum dots; first is cylindrical, and the second is conic. The density of states in the first quantum dot (1601) is chosen to match the density of states in the analyte. In this case the analyte is a detectable portion of a DNA. This will allow charge transport between the DNA and the cylindrical nanostructure (1601). The second quantum dot (1602) is designed so that the density of states of that quantum dot does not match the density of states of the same portion of the DNA. Thus, the charge transfer between that quantum dot and DNA will not happen, regardless of the fact that this quantum dot has the same functionalization as the first quantum dot, and that it attracts and bins the same portion of the DNA, as it is illustrated in the figure. In both cases the complementarity between the DNA and oligonucleotide is satisfied, but the charge transfer between the DNA and the nanostructure will happen only if simultaneously the density-of-states distribution between the nanostructure and the targeted DNA is also matched. This gives an additional degree of selectivity for the detection of the species. In the same figure there is also third quantum dot (1603) which has the functionalization which is not complementary to the targeted portion of the DNA. So there will be no hybridization and no binding between this quantum dot and the DNA. The charge transfer for this reason will not happen between this quantum dot and the DNA.

One can note that although the oligonucleotide on the first and the second nanostructure may be the same they still could detect different molecules, if the density of states in the first and second nanostructure are different. For example, the oligonucleotide will attract and bind the same type of the molecule, but the charge or/and energy transfer will occur only between the molecule which has density of states that overlaps with the density of states of the nanostructure. The quantum dot which has the same functionalization but different density of states from the analyte will not register any charge or/and energy transfer. This demonstrates how the quantum confinement increases the selectivity. It also shows that in some cases the functionalization can be replaced by the quantum confinement. Because different portions of the array have different density of states and are designed to detect charge and/or energy transfer between different portions of the DNA, one can imagine not functionalized array of nanostructures which can be used for the DNA sequencing.

The combination of the nanostructure size, shape or/and distances between the nanostructures and the functionalizations can also be chosen. So, when oligonucleotide attached to the nanostructure hybridizes to a specific nucleic acid, a detectable change in charge transfer occurs.

Figure 17:
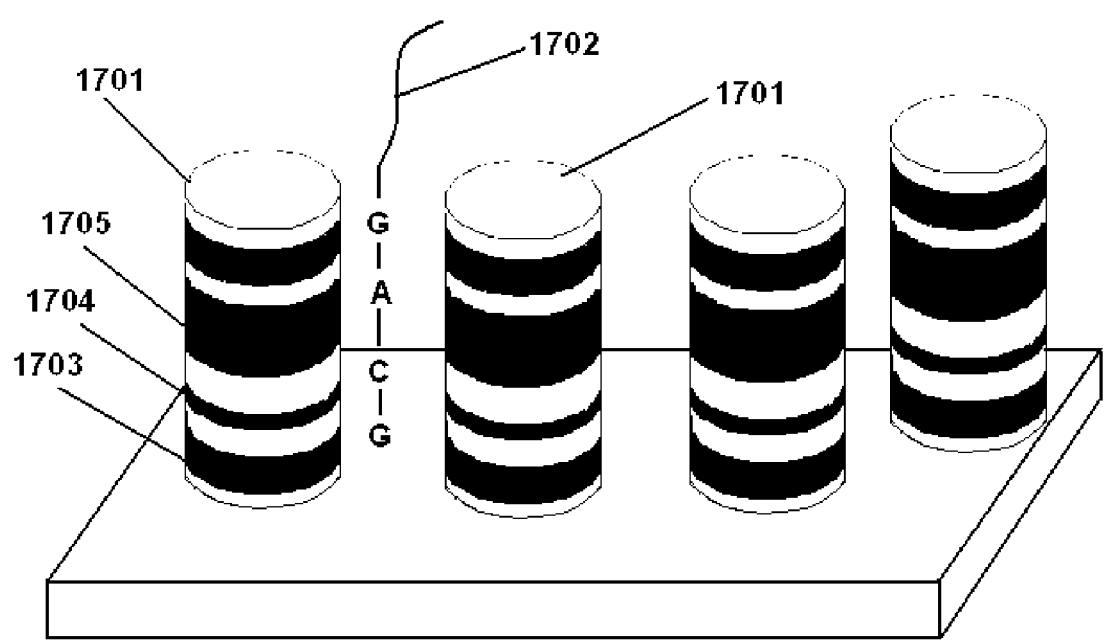
FIG. 17 presents the situation where quantum dots (1701) are built from a number of layers of thin films or number of superlattice layers (1703, 1704, and 1705). The each part of the quantum dots is designed to have the density of states that corresponds to the density of states of a part of the analyte. For instance the density of states of the part (1703) corresponds to the density of states of the "G" part of the analyte (1702), while the part (1705) corresponds to the part "A" of the analyte. The charge or/and energy transfer between the nanostructures and the analyte will be maximal only when an analyte (1702) that has segments with the same density of states as the densities of the states of the nanostructure segments is aligned to the nanostructure.

In an embodiment, the combination of nanostructures may be used. For instance, FIG. 17 presents the situation where combination of quantum dots and thin films or superlattices is used to build quantum dots (1701) from a number of layers of thin films or number of superlattice layers (1703, 1704, and 1705) and so on. The dimensions of the quantum dots can be for instance, just as an example, 5 to 50 nm in radius and 50 nm in height, but the thickness of one layer of the superlattice from which the quantum dot is build can be just as thin as, for instance, a few Angstroms. Quantum dots or some other nanostructure may be build from thousands of such layers. Each of the superlattice layers which are used to build quantum dots can be made from different material; for instance, they can be built from materials with different work functions. In this example, when such superlattices or thin films that comprise different work function materials are exposed to the light, they will be charged differently. The thickness of each superlattice or thin film layer (1703, 1704, and 1705) can be different, so that each thin film layer or superlattice will have different density-of-states distribution due to the confinement. The spacing between films can be done so that the charge distribution attracts or pushes away specific analyte (1702). An array of such thin film or superlattice composites can be built and each quantum dot in that array can be attached to a different electrical potential, exposed to different electromagnetic field and/or exposed to a light of different wavelengths. The electronics that bring bias on the quantum dots can also sense the transfer of charges or/and energy between the quantum dots and the analyte (1702) or charge and/or energy transfer caused change of the capacitance or any other electrical characteristic of the quantum dots (or group of quantum dots when an analyte (1702) is present or it is in the close vicinity of a quantum dot or it is between them).

As one example, the said thickness of the superlattices and/or thin films is chosen so that on the edges of the quantum dots which contain a multilayers of these films, specific base sequence (Adenine, Thymine, Guanine, Cytosine) of DNA or RNA will bind on the edges of these supperlattices or/and thin films. When the binding occurs, the charge or/and energy transfer between the superlattice or film and the bases of bind DNA or the change in a measured electrical signal related to that quantum dot or group of quantum dots will occur. Each of the bases (A, T, G, C) has a specific charge arrangement and specific charge bonding with a specific energy level. So, the binding of the bases will be specific and the charge and/or energy transfer will occur only when the energy level density distribution in the particular level of the supperlattice or/and film overlaps with the energy level density distribution in the bind base. See for instance FIG. 17.

Figure 18:
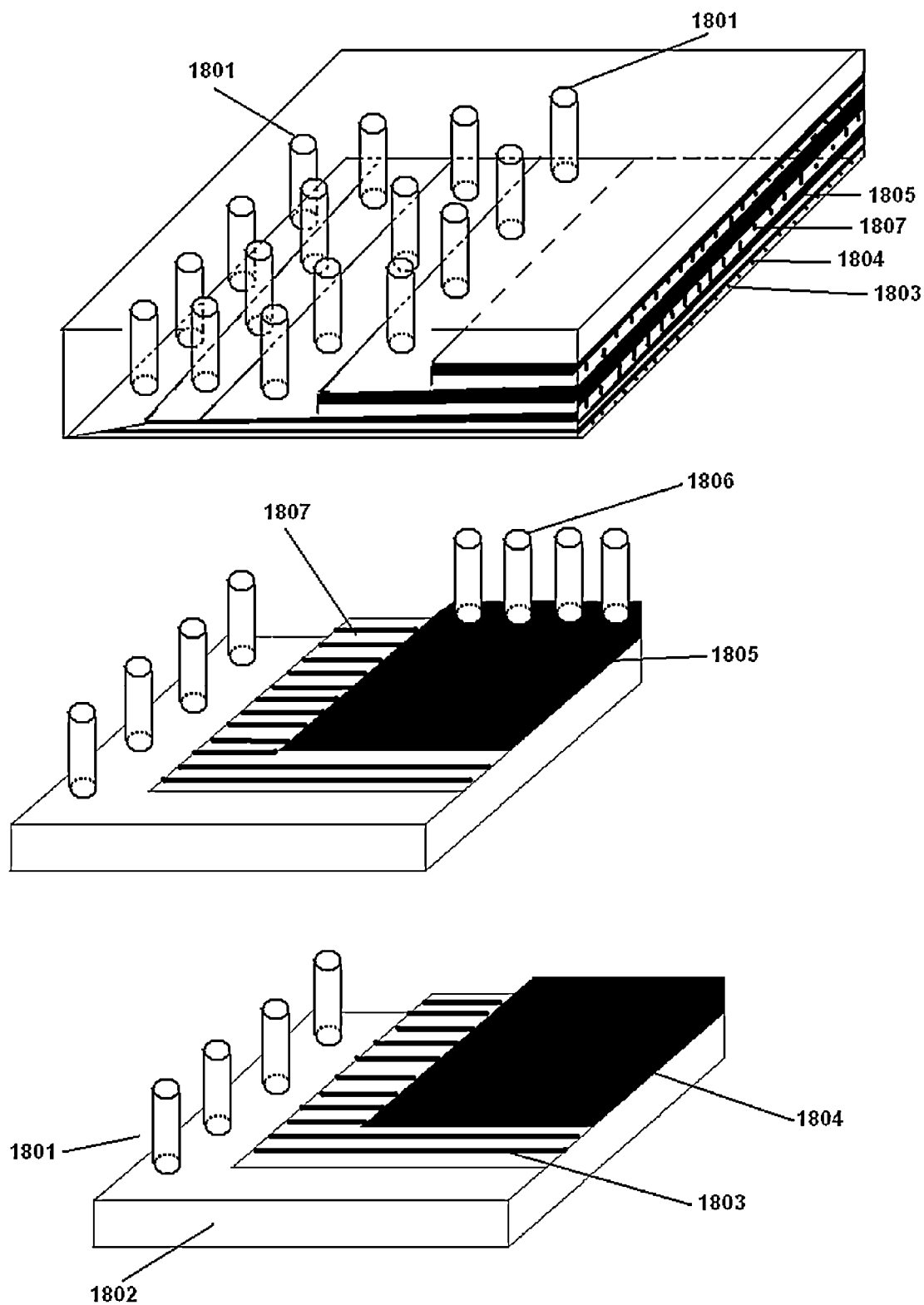
FIG. 18 presents formation of the quantum dots (1801) on a conductive thin film (1803) deposited on the substrate (1802). The conductive thin film (1803) is isolated by the thin film (1804, 1807) from other thin films and other quantum dots. The second set of quantum dots (1806) is connected to another conductive thin film (1805), which is again isolated from other thin films and other quantum dots, and so on. When the targeted analyte is present, the different specific analyte will interact, exchange charges and/or energy with the different set of the quantum dots. Since separate sets of the quantum dots are connected to the separate thin films, each group of the quantum dots will send signal to the different thin film layer. Because the different thin film layers are connected to different electronics channels, knowing the combination of the thin films that conducted the signal, one can tell the precise spatial position of the quantum dots that produced the signal. On this way one can locate the targeted analyte and also can specify the analyte.

Another combination of nanostructures could be a formation of the quantum dots on the layers of thin films; see FIG. 18. On one layer of thin film (1801), which can be, for instance, conductive and just a few Angstroms thick, deposited is one set of quantum dots (1802). In the second step, that layer of thin film is connected by the electronics (1803) and covered by isolator film (1804). In the following step new layer of the conductive thin film is deposited (1805) over the previously deposited electrically isolating film (1804). On that layer new set of quantum dots (1806) is deposited in a line, for instance, perpendicular to the first line. This new set of quantum dots may or may not be different from the first set of quantum dots. This layer is now connected to the new channel of electronics (1807) and covered by isolator film. The process can continue further by deposition of new conductive film and new set of quantum dots, new line of quantum dots, which again can have different orientation then previously deposited quantum dots. Note that the height of quantum dots is much larger than total thickness of all layers of the film together. So, the quantum dots are going through the layers of the films. When the targeted analyte is present, the different set of the quantum dots will send signal to the different thin film layer for the different specific analyte. Since the different thin film layers are connected to different electronics channels, knowing the combination of the thin films which conducted the signal one can tell the precise spatial position of the quantum dots that produced the signal and can locate the targeted analyte. Also knowing the density distribution of energy levels that are specific for the quantum dots that produced the signals, one can make further specification of the analyte. Note that this method gives possibility to significantly reduce the number of the connections between the quantum dots and the electronics, and at the same time gives an accurate location of the signal.

Figure 19:
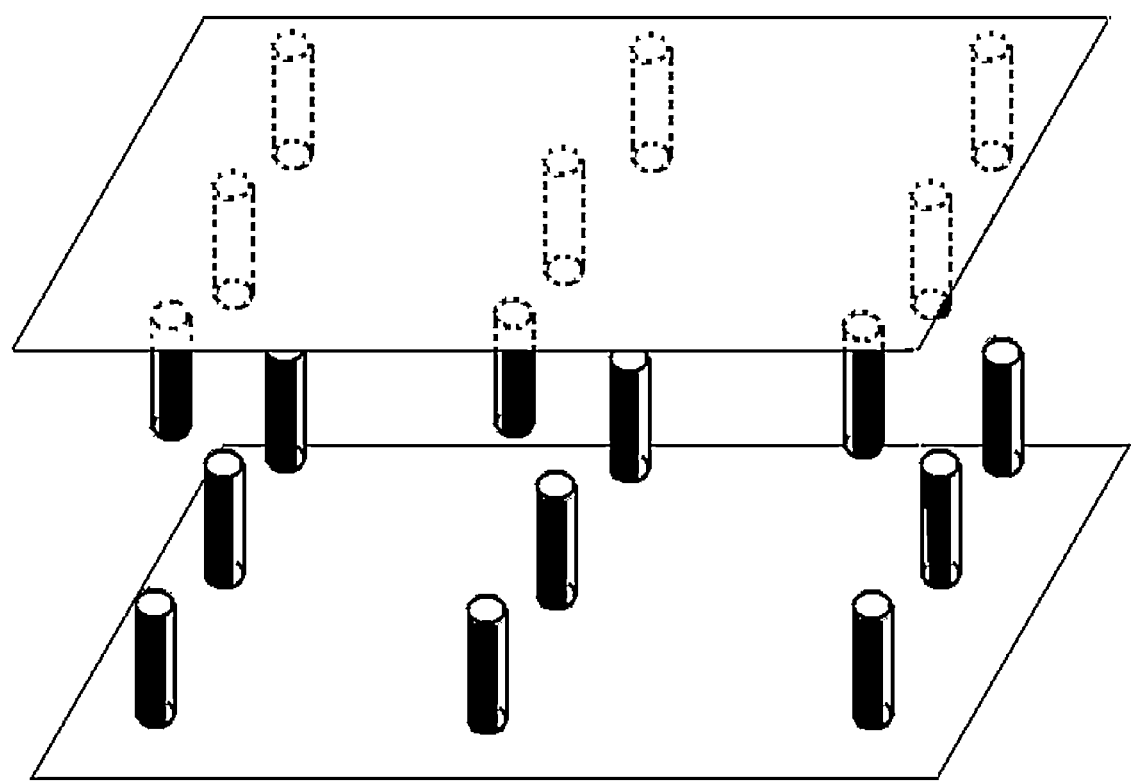
FIG. 19 presents three dimensional structure constructed from two sets of two dimensional nanostructure arrays placed close to each other in some kind of sandwich like structure, so that the quantum dots will touch or/and almost touch each other and make a three-dimensional structure with shape similar to channels going between the quantum dots.

The nanostructures may have two-dimensional (arrays) or three-dimensional configurations. One can also imagine that two or more two-dimensional configurations form three dimensional structure. For instance, two sets of two dimensional arrays can be placed close to each other in some kind of sandwich-like structure so that the quantum dots will touch or/and almost touch each other and make the three-dimensional structure. One possible three-dimensional structure may have shape similar to channels going between the quantum dots; see FIG. 19. One can imagine that variety of three dimensional configurations can be made with this sandwich-like approach of using two arrays of two-dimensional quantum dots. Two dimensional quantum dot structures that will be the building blocks of three dimensional-structures can have different shapes and different two-dimensional distributions.

The above description of making three-dimensional structure using two-dimensional nanostructure arrays is given here just as an example. It is clear that variety of real three dimensional structures can be made using variety of combinations of nanostructures, such as quantum dots, wires, nanotubes, superlattices, and thin films.

The array of quantum dots comprised from several layers of superlattices or thin films can be, for instance, produced in a following way. The layers of superlattices or thin films are deposited each on a substrate. Each layer of the film and/or superlattice can have different thickness to achieve desired density of states by quantum confinement. For instance, from thousands to hundreds of thousands layers can be deposited over each other, each having different composition and thickness, if needed. In the next step, surface (outside portion of the circle below the quantum dots) is removed by photolithography, computerized atomic force microscope, and plasma ion etching of the parts. This process would, for instance, form cylindrical quantum dots with multiple thin film layers.

Figure 20:
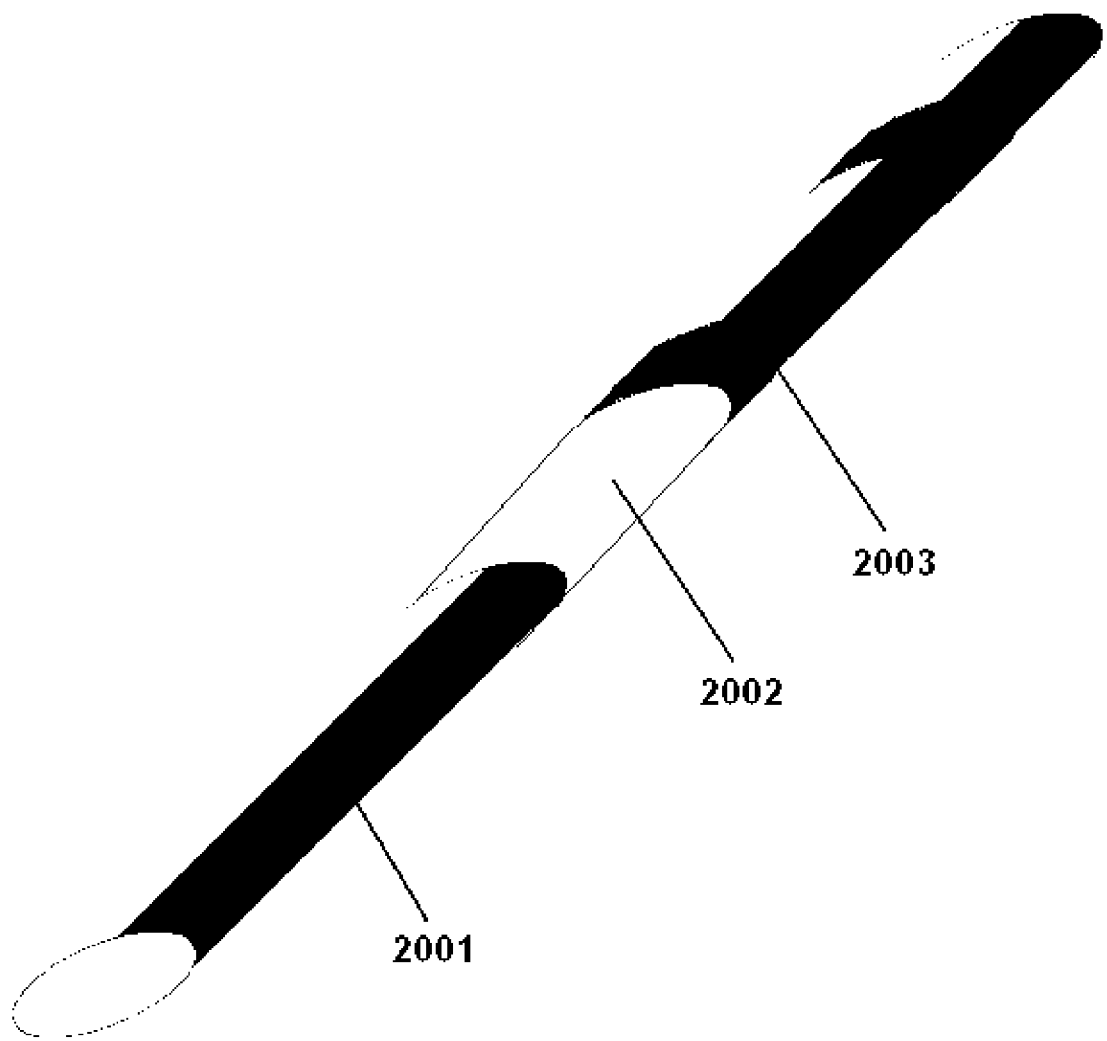
FIG. 20 presents a nanotube (but it can also present a nanowire) that contains multi parts (2001, 2002, 2003). Each part of the nanotube (nanowire) (2001, 2002, 2003) may have different length and composition, and may be designed to sense different analyte or different part of the analyte (because it may be designed to have different density of state that corresponds to the targeted analyte or the targeted part of the analyte).

The nanotubes which contain multi parts may be formed in a similar way. For example, see the nanotubes shown in FIG. 20; each part (2002) and (2003) of a nanotube (2001) may have different length and composition. By photolithography or atomic force microscope and the plasma ion etching, an inner part of the circle can be removed and the nanotube can be formed. There are also other possible methods. For instance, we can first form the nanorods, follow that by the deposition of film layers or superlattices and then remove nanorods. Also there are methods for making uniform size holes and create nanotubes by high energy beams.

Using combination of nanostructures, such as supperlattices, thin films, quantum dots, quantum wires, nanotubes, etc., one can imagine that variety of the two and three dimensional structures can be formed, and that above models serve just as possible examples.

The distribution of the energy levels in the detector nanostructures in addition to the nanostructure design, such as size, shape and composition can be also controlled by outside applied fields, such as magnetic field, electromagnetic field, applied electrical voltage, temperature, pressure, acoustic waves, and light. These external factors will consequently affect the charge transfer between the analyte and the device. However, these external factors can also be used to initiate the charge transfer, for instance, to excite energy of charges in the targeted analyte above needed threshold required for the charge transfer to happen. One can imagine such a device where the light with specific energy (wavelength) is applied to the targeted analyte to extract the charges from the analyte and to initiate charge transfer. The timing between the applied light and the measurement of the charge signal can be also changed.

One can imagine the device in which in addition to the frequency and time duration of the applied electromagnetic field, the voltage or the applied light can be changed during the experiment to initiate charge or/and energy transfer or to discriminate the signals from different analytes. One can also imagine changing the temperature of the analyte or applying the magnetic field in the same time, or applying any combination of these external factors in the same time or in any time order as well as applying all of them in the same time.

One can imagine the method in which the charge or/and energy transfer between the nanostructure and the analyte or between the nanostructures or between the analytes is initiated by changing the frequency of applied electromagnetic field. The electronics registers the signal when the charge or/and energy transfer occur(s). Note that in this case there is no need to measure the charge transfer; only the energy transfer can be registered. The process can be compared with that in NMR. There are density of states in the nanostructure and the density of states in the analyte which overlap. The externally applied electromagnetic field will cause charge or energy transfer between nanostructure and analyte, or between the nanostructures when analyte is present, or between the analytes when analytes are close to the nanostructure. The electronics will register the energy transfer, similarly to how it registers energy transfer in NMR when transfer between two states happens.

One can also imagine that in the addition to measurement of the charge transfer other physical observables can be measured too, in the same time or in any time combination. For instance, one can measure charge transfer in the combination with the photoluminescence or in the combination with the measurement of time of flight of electrolyte from one nanostructure to another, when magnetic field is applied or not and when temperature is changed or not. By combining results from different experiments one can give more accurate interpretation of the results. For instance, by comparing photoluminescence signals from the quantum dots with the specific energy level distribution one can get confirmation about the energy states in the targeted analyte using spectroscopy and the electrical measurements. Said measurement of the time of flight, and applied magnetic field can give additional information about the mass and about the viscosity, etc.

Consequently, applying the described method of quantum confinement to the existing methods, such as electrophoresis, photoluminescence, fluorescence spectroscopy, time of flight, ion mobility, spectrometry, etc., one can greatly improve selectivity of these methods.

Biological molecules are generally charged, so they could also be manipulated using voltage bias applied on the detectors nanostructures. This can also increase the process of selecting and grouping the targeted analyte on the detector array prior to applying for instance photoluminescence.

The charge and/or energy transfer may be also obtained from a nanostructure to the analyte. Again, using the quantum confinement this charge transfer may be selective, happening only when the quantum confinement is satisfied. After receiving the charge transfer the analyte may be then manipulated further. Additional fields can separate or/and transport such charged analyte. Alternatively, some other methods may be used to detect such charged analyte, for instance, any spectroscopic or time of flight methods.

There are many known ways to produce nanostructures with controlled shape and size. For instance, quantum dots may be produced by ion implantation, pulsed laser deposition, pulsed electron deposition, from chemical precursor, by photolithography, plasma ion etching, etc. For instance, by applying the pulsed laser deposition one can produce quantum dots of different sizes which will decrease from the center of the laser plume toward the edges. The good examples of size-controlled variety of quantum dots include the size selected Si and InAs quantum dots produced with picosecond pulsed laser deposition. See, e.g. M. H. Wu, R. Mu, A. Ueda, D. Henderson, and B. Vlahovic, Micro Raman Spectroscopy of Silicon Nanocrystals Produced by Picosecond Pulsed Laser Ablation, Mat. Res. Soc. Symp. Proc. 738, G12.2.1, 1-5. 2003. D. O. Henderson, R. H. Wu, R Mu, and A. Ueda, B. Vlahovic, M. Jaksic, Fabrication of Self-Assembled, Size-Graded Si Quantum Dots by Pulsed Laser Deposition, MRS Meeting, San Francisco, Apr. 21-25, 2003. H. Wu, R. Mu, A. Ueda, D. O. Henderson, and B. Vlahovic, Micro Raman Spectroscopy of Silicon Nanocrystals Produced by Picosecond Pulsed Laser Ablation, MRS Meeting, San Francisco, Apr. 21-25, 2003.

Figure 21:
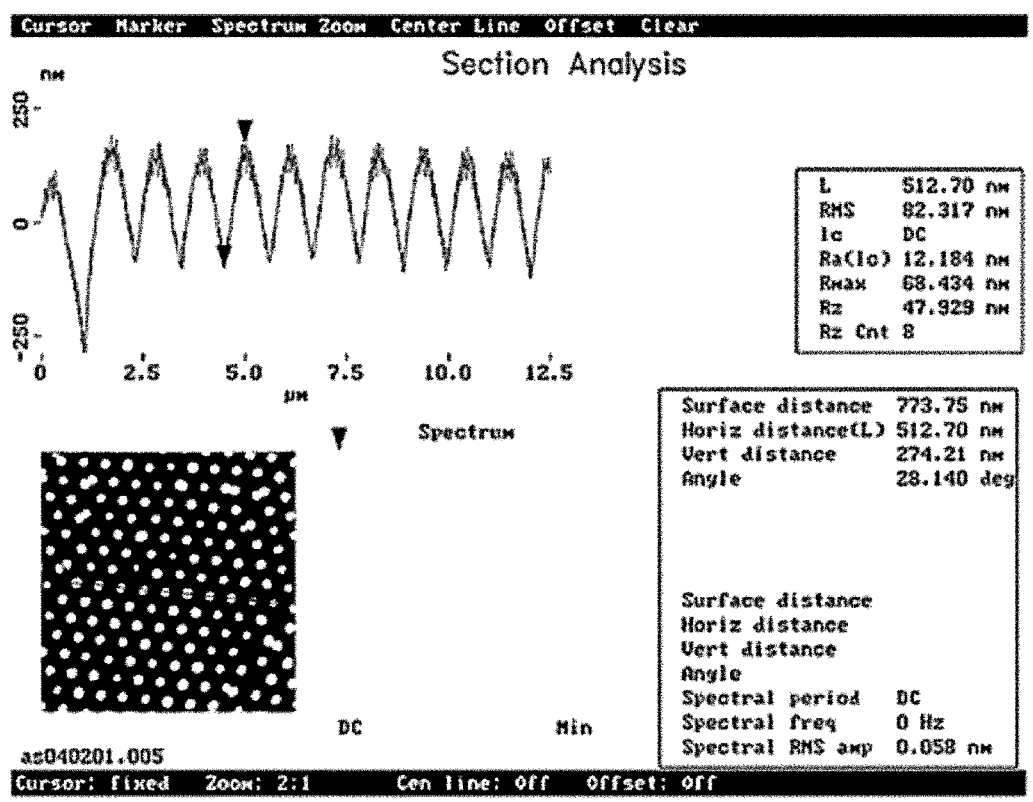
FIG. 21 shows AFM image of CdSe quantum dots produced by ion implantation of Cd at 450 keV followed by ion implantation of Se at 330 keV. These implantation parameters insured an overlap of the Se and Cd depth profiles, with the peak of the profile at ~200 nm. By subsequent annealing at 400° C. to 1000° C. for one hour CdSe nanocrystals are formed.

The quantum dots can be also produced inside substrate. Ion implantation provides a direct way of fabricating quantum dots in dielectric hosts. Ion beams are isotopically clean and therefore do not have the inherent impurities which are present in chemical synthesis. Moreover, ion implantation is not constrained by the equilibrium thermodynamics which limits how much quantum dot material can be incorporated in a melt phase (e.g. dissolving CdSe in a glass). Ion implantation is a brute force method which circumvents the constraints imposed by equilibrium thermodynamics; we simply add as much material as desired, which exceeds the amount that could be introduced from the melt phase. Under this condition we have a supersaturated solid solution that is meta-stable. Annealing the meta-stable system causes the formation of quantum dots at concentrations that could not be achieved by synthetic chemical routes. As example illustrated is implantation of Cd followed by Se to affect the formation of CdSe quantum dots. The implantation parameters are as follows: 1) Implanted Cd at 450 keV at ion doses of $1 \times 10^{16}$, $3 \times 10^{16}$, $6 \times 10^{16}$ and $1 \times 10^{17}$ ions cm$^2$. 2) Implanted Se at 330 keV at ion doses of $1 \times 10^{16}$, $3 \times 10^{16}$, $6 \times 10^{16}$ and $1 \times 10^{16}$ ions cm$^2$. These implantation parameters insured an overlap of the Se and Cd depth profiles. The peak of the profile is at ~200 nm and the FWHH is also ~200 nm. The implanted samples were later annealed at 400° C. to 1000° C. for one hour in 5% hydrogen+95% Ar atmosphere. These are the annealing conditions used previously for growing Se, Cd and CdSe nanocrystals for these ions implanted in the silica windows. These annealing conditions promoted diffusion of the implanted ions, which in turn lead to nucleation. Once a critical nucleus is formed, the nanocrystals will begin to grow; the ultimate size will depend on the annealing time. Included is AFM image, of such produced quantum dots FIG. 21, D. O. Henderson, R. Mu, M. H. Wu, A. Ueda, A. Meldrum, C. W. White, M. Jaksic, and B. Vlahovic, The Optical Properties of Selenium Nanocrystals Fabricated by Ion Implantation, *Proceedings of MRS Spring Meeting*, April 21-25, San Francisco, 2003. D. Denmark, A. Ueda, C. L. Shao, M. H. Wu, R. Mu, C. W. White, B. Vlahovic, C. I. Muntele, D. Ila, and Y. C. Liu, Indium phosphide nanocrystals formed in silica by sequential ion implantation, accepted for Surface & Coatings Technology (2004).

For quantum dots produced from chemical precursors, the size can be controlled by controlling the surface tension.

The methods of quantum dots functionalization is well described, for instance, in H. Lee US 2005/0017260, A Mirkin et al. U.S. Pat. No. 6,828,432 B2 and references therein.

There are also well known methods for fabrication of other nanostructures, for instance, nanotubes with uniformly controlled inner diameter from 1-100 nm and functionalization of inner and outer surfaces, which are chemically stable and can have variable controlled length and desired electrical characteristics (insulating, semiconducting, metallic). At least one group has been using the tubular structures prepared using porous alumina as template for biological separation. The other group is using semiconductor nanowires as templates for formations of nanotubes; see for instance P. Yang, US 2004/0262636A1.

The electronics required to complete described nanosensor device is also well known. As it is illustrated in the FIG. 1, nanostructures can be connected to the multichannel amplifier which can be further connected to other electronics, for instance, triggers and coincidence electronics, controllers, and finally computer, which may control entire process of data acquisition and analysis.

A sample device that comprises the metallic microstrips on Si substrate and nanostructures, semiconductors quantum dots, placed between the microstrips is shown on FIGS. 22a, 22b, and 22c. The microstrips (2204) are separated for 50 microns, and each of the microstrips is connected with the golden wires (2205) to the separate channel of VA chip (2206), which amplifies the signals from microstrips and also provides the bias for the microstrips and nanostructures (2203). The chip also allows external triggering and timing with the other equipment and external electronics and it is further connected through wires (2207) and connector (2208) with the data acquisition system. When an analyte is above the nanostructure, in this example quantum dots (2203) or in the contact with the quantum dots the microstrips associated with that quantum dots send the signal to the electronics. The signal is different if there is an overlap between the density of states in the quantum dots and the analyte or if there is no any overlap between the density of states of the quantum dots and the analyte. On FIG. 22c shown is AFM image of quantum dots (2203) produced by pulsed laser deposition on Si substrate. On FIG. 22b different symbols (circles, triangles, squares, and pentagons) are used for quantum dots (2203) to emphasize that each group of the quantum dots placed between two microstrips has different sizes or shapes and therefore different density of states.

One can use earlier described calculations to design: the size, composition and geometry of the substrate; nanostructure's core and shell; ligands, and externally applied fields (such as bias, light, magnetic field, temperature, pressure, etc.). However, one can also create the database, which will include effects of all the above parameters on the interaction between the nanostructures and analytes. Using the database, the initial design of nanostructures based on the calculations can be further improved by making the comparisons with the experimental data. In the analysis of the plurality of the data obtained (for instance, an array of thousands of quantum dots), a computer can compare the signals for different quantum dots with tabulated experimental data. The comparison will take into account applied external parameters, which will result in the identification of the targeted analyte, its composition, structure, etc.

It is worth nothing that it is not necessary to know exact values or distribution of the energy levels in the targeted analyte. An array of the nanostructures with a plurality of the energy levels can be created, for instance, quantum dots with broad variety of the charge energy levels, specific shapes, compositions, distances, applied magnetic or electromagnetic fields. The parameters can be calculated prior to the formation, so that the range of the energy levels in the nanostructures overlaps with the targeted range of the energy levels in the analytes for which the detection system is designed. The calibration of the device can be made in such a way that a known analyte is introduced into the device. The record can be kept of particular nanostructure-analyte interaction, i.e. for instance which quantum dots will register a charge transfer. Then the different analyte can be introduced and again measurements can be done to determine which quantum dots are now experiencing interaction (charge transfer with the targeted analyte). The process can continue and the database of the nanostructure responses to the introduced specific analytes can be made. When unknown analyte or plurality of unknown analytes is introduced into the device to be analyzed, knowing which nanostructures have received signals will tell us over which part of the device is a particular analyte.

The DNA sequencing can be done in the same way. Once it is established which part of the nanostructure is responsible for which base, knowing which structure is having signals will give information about the base which is associated with that nanostructures. By knowing the nanostructure or the combination of the nanostructures that have signal and by monitoring how the signal(s) change in time, one can reconstruct the order of the bases in the DNA and complete the DNA sequencing. The effect of the external fields can also be monitored and recorded.

In a similar way calibration of the device can be used, for instance, for separation of analyte. The different electrical bias (DC or AC) or electromagnetic field or any other physical variable can be applied on the device which contains known analyte placed over the nanostructures. The effect of the particular combination of voltage, electrical fields, light magnetic fields etc. can be then observed and recorded. The created database can be used to apply necessary physical variable or combination of the variables to create desired effect on the analyte, such as its motion, separation, extraction etc.

While the present invention has been described with references to the specific examples thereof, it should be understood by these skilled in the art that various modifications and variations can be made and equivalents may be substituted to the present invention without departing from the true spirit and the scope of the invention. It is intended that the present invention covers modifications and variations of this invention provided they come in the scope of the appended claims and their equivalents. Many modifications may be made to adopt a particular situation, material, composition of matter, methods, process step or steps, to the objective spirit of the invention.

What is claimed is:

1. Method for detection, determination of structure, separation, transport, extraction, and control of biological and/or chemical materials based on the process consisting essentially of:
   determining an energy level or an energy state distribution of an analyte;
   building a nanostructure or a plurality of nanostructures;
   adjusting a material composition, shape and size of the nanostructure or the plurality of nanostructures to produce the energy level or energy level distribution;
   arranging the nanostructure or plurality of nanostructures in an array;
   the energy state distribution over the array being the same as the analyte being detected;
   electrically connecting the nanostructure or plurality of nanostructures to electronics for monitoring the charge and/or energy transfer between the analyte and the nanostructures or plurality of nanostructures;
   wherein the charge or energy transfer occurs between the analyte and the nanostructure or plurality of nanostructures only when the energy level or energy state distribution of the analyte is substantially identical to that of the nanostructure or plurality of nanostructures.

2. Method of claim 1, wherein nanostructure is any combination of superlattices, quantum dots, quantum wires, nanotubes, nanopores, thin films, or photonics crystals.

3. Method of claim 1, wherein targeted analyte(s) may be any chemical elements, compounds, molecules, bio molecule, bio agents, nucleotides, genes, nucleic acids (natural or synthetic), viral RNA and DNA, bacterial DNA, fungal DNA, cDNA, mRNA, DNA and RMA fragments, PNA (peptide nucleic acid), DNA (both genomics and cDNA), RNA or hybrid (where the nucleic acid contains any combination of deoxyribo and ribonucleotides, and any combinations of bases), single base pairs of DNA and RNA, proteins, various toxins, fungi, parasites, *Rickettsia*, microbial cultures, viruses, bacteria, or uniquely identifiable components of byproducts, and oligonucleotides.

4. Method of claim 1, wherein the nanostructure has inner and/or outer shell(s).

5. Method of claim 1, wherein the nanostructure core or/and nanostructure shell is functionalized by a ligand, wherein said ligand has sequences complementary to the sequences of targeted analyte, said ligand comprises at least one type of recognition oligonucleotides, and each type of recognition oligonucleotide comprises a sequence complementary to at least one portion of sequence of targeted analyte, and/or said one portion of the targeted nucleic acid.

6. Method of claim 1, wherein the nanostructure shape is adjusted to be similar or complementary to the analyte.

7. Method of claim 1, wherein the spacing between the nanostructures is adjusted to enhance or decrease charge and/or energy exchange between analyte and nanostructures.

8. Method of claim 1, wherein the nanostructure may be arranged in two dimensional arrays or/and three dimensional structures.

9. Method of claim 1, further comprising AC and/or DC electrical biases applied on the nanostructure and/or the analyte, the frequency of AC can vary from 1 Hz to THz and can be combined with DC, the biases can be continuous or/and pulsed.

10. Method of claim 1, further comprising light source(s) applied on nanostructure and/or analyte.

11. Method of claim 1, further comprising electromagnetic fields, magnetic fields, temperature, acoustic waves and pressure applied on the nanostructure and/or analyte.

12. Method of claim 1, further comprising any combination of electrical biases, light sources, electromagnetic fields, magnetic fields, temperature, acoustic waves and pressure applied on the nanostructure and/or analyte.

13. Method of claim 12, further comprising a coincidence circuit configured to generate coincident detection signal in the response to the coincidence between the said charge transfer at the nanostructure and the applied light source, or/and coincidence between any combination of the applied fields: magnetic field, electromagnetic field, temperature, electrical bias, light source, and pressure.

14. A method for detecting biological and/or chemical materials, further comprising: a method described in claim 13; exposing said device to said analyte, biological and/or chemical material; applying electrical AC and/or DC bias to the sensor nanostructure; detecting and monitoring the charge and/or energy transfer between the analyte and nanostructure or/and between the nanostructures.

15. A method for separation and extraction of biological and/or chemical materials, further comprising: a method described in claim 13; exposing said device to said analyte, biological and/or chemical material; applying electrical AC and/or DC bias to the sensor nanostructure; separation or/and extraction and/or transport of the chemical or/and biological material by applied electrical bias to the specific part of the nanostructure, or specific area or volume of the nanostructures or detecting system.

16. A method as claimed in claim 15, wherein said separation of material is activated or/and enhanced or/and conducted by optically illuminating nanostructure and/or analyte, by applying AC or/and DC, magnetic fields, by applying electromagnetic fields, by applying temperature, by applying pressure, or/and by applying any combination of these effects.

17. A method as claimed in claim 16, wherein release of biological and/or chemical materials is controlled.

* * * * *